US012734222B2

(12) United States Patent
Li

(10) Patent No.: US 12,734,222 B2
(45) Date of Patent: Sep. 15, 2026

(54) METHOD AND MEDICINE FOR TREATING HUNTINGTON'S DISEASE

(71) Applicant: Talengen International Limited, Hong Kong (CN)

(72) Inventor: Jinan Li, Beijing (CN)

(73) Assignee: Talengen International Limited, Hong Kong (CN)

( * ) Notice: Subject to any disclaimer, the term of this patent is extended or adjusted under 35 U.S.C. 154(b) by 749 days.

(21) Appl. No.: 17/914,275

(22) PCT Filed: Mar. 24, 2021

(86) PCT No.: PCT/CN2021/082725

§ 371 (c)(1),
(2) Date: Sep. 23, 2022

(87) PCT Pub. No.: WO2021/190563

PCT Pub. Date: Sep. 30, 2021

(65) Prior Publication Data

US 2023/0141921 A1 May 11, 2023

(30) Foreign Application Priority Data

Mar. 24, 2020 (CN) ......................... 202010213463.1

(51) Int. Cl.
*A61P 25/28* (2006.01)
*A61K 38/48* (2006.01)
*A61K 45/06* (2006.01)
*A61P 25/14* (2006.01)

(52) U.S. Cl.
CPC ............ *A61K 38/484* (2013.01); *A61K 45/06* (2013.01); *A61P 25/28* (2018.01)

(58) Field of Classification Search
CPC ......... A61K 38/484; A61P 25/28; A61P 25/14
See application file for complete search history.

(56) References Cited

U.S. PATENT DOCUMENTS 6,471,960 B1 10/2002 Anderson
7,074,402 B2 * 7/2006 Griffin ............... A61K 38/4866 514/17.7
8,841,329 B2 9/2014 Shi et al.
10,709,771 B2 7/2020 Li
11,090,372 B2 8/2021 Li
11,207,387 B2 12/2021 Li
11,389,515 B2 7/2022 Li
11,400,142 B2 8/2022 Li
11,478,535 B2 10/2022 Li
11,547,746 B2 1/2023 Li
11,642,397 B2 5/2023 Li
2005/0250694 A1 11/2005 Ma
2006/0104969 A1 5/2006 Oray et al.
2014/0044796 A1 2/2014 Kehrel et al.
2014/0186423 A1 7/2014 Gelfand
2018/0360930 A1 12/2018 Li
2018/0369345 A1 12/2018 Li
2019/0015485 A1 1/2019 Li
2019/0328849 A1 10/2019 Li
2019/0328850 A1 10/2019 Li
2019/0343931 A1 11/2019 Li
2019/0351033 A1 11/2019 Li
2019/0359723 A1 11/2019 Wang et al.
2020/0078449 A1 3/2020 Li
2020/0085920 A1 3/2020 Li
2020/0206324 A1 7/2020 Li
2021/0154275 A1 5/2021 Li
2022/0218799 A1 7/2022 Li
2023/0066726 A1 3/2023 Li
2023/0081922 A1 3/2023 Li
2023/0084586 A1 3/2023 Li
2023/0139956 A1 5/2023 Li
2023/0143354 A1 5/2023 Li
2023/0173039 A1 6/2023 Li
2023/0181699 A1 6/2023 Li
2023/0190891 A1 6/2023 Li
2023/0302102 A1 9/2023 Li
2023/0346897 A1 11/2023 Li
2024/0000903 A1 1/2024 Li
2024/0000904 A1 1/2024 Li

FOREIGN PATENT DOCUMENTS

CA 3008686 A1 6/2017
CA 3167202 A1 8/2021
CN 1784241 A 6/2006
CN 101886066 A 11/2010
CN 102154253 A 8/2011
(Continued)

OTHER PUBLICATIONS

Farmer et al. Huntington's Disease: A Therapeutic Update. Practical Neurology. 2017;46-48.*
Kaur et al. Tetrabenazine: Spotlight on Drug Review. Ann Neurosci. 2016;23:176-185.*
Altner et al. Extending the Phenotypic Spectrum of Huntington Disease: Hypothermia. Mol Syndromol. 2020;11:56-58.*
Miranda et al. Body composition and bone mineral density in Huntington's disease. Nutrition. 2019;59:145-149.*
Extended European Search Report, dated Mar. 7, 2023, for European Patent Application No. 21776691.4, 16 pages.
U.S. Appl. No. 18/037,299, filed May 16, 2023, Li, Jinan (Copy not submitted herewith pursuant to the waiver of 37 C.F.R. 1.98(a)(2)(iii) issued by the Office on Sep. 21, 2004).
(Continued)

*Primary Examiner* — Lynn Y Fan
(74) *Attorney, Agent, or Firm* — Morrison & Foerster LLP

(57) ABSTRACT

Provided are a method and drug for treating Huntington's disease, which includes: administering a therapeutically effective amount of a component of a plasminogen activation pathway or a related compound thereof to a subject. Also provided are a drug, pharmaceutical composition, product, and kit used for treating Huntington's disease and containing the above component or compound.

15 Claims, 8 Drawing Sheets

Specification includes a Sequence Listing.

(56) References Cited

FOREIGN PATENT DOCUMENTS

| | | | | |
|---|---|---|---|---|
| CN | 103191155 A | | 7/2013 | |
| CN | 108210910 A | | 6/2018 | |
| CN | 108210916 A | * | 6/2018 | ............ A61K 38/48 |
| CN | 109066567 A | | 12/2018 | |
| CN | 109125715 A | | 1/2019 | |
| CN | 109925507 A | | 6/2019 | |
| CN | 107603951 B | | 8/2020 | |
| CN | 111905103 A | | 11/2020 | |
| EP | 4122481 A1 | | 1/2023 | |
| EP | 4122488 A1 | | 1/2023 | |
| EP | 4248954 A1 | | 9/2023 | |
| EP | 4249504 A1 | | 9/2023 | |
| JP | 2019-500423 A | | 1/2019 | |
| JP | 2019-500424 A | | 1/2019 | |
| TW | 201722465 A | | 7/2017 | |
| TW | 201722467 A | | 7/2017 | |
| TW | 201906627 A | | 2/2019 | |
| TW | 202227472 A | | 7/2022 | |
| WO | 2001/24815 A1 | | 4/2001 | |
| WO | 2001/58476 A2 | | 8/2001 | |
| WO | 2001/62799 A2 | | 8/2001 | |
| WO | 200156532 A2 | | 8/2001 | |
| WO | 2003/071267 A1 | | 8/2003 | |
| WO | WO-2003066842 A2 | * | 8/2003 | .......... C12N 9/6435 |
| WO | 2004/111226 A1 | | 12/2004 | |
| WO | 2017101867 A1 | | 6/2017 | |
| WO | 2017101868 A1 | | 6/2017 | |
| WO | 2017101870 A1 | | 6/2017 | |
| WO | 2018107684 A1 | | 6/2018 | |
| WO | 2018107685 A1 | | 6/2018 | |
| WO | 2018107688 A1 | | 6/2018 | |
| WO | 2018107689 A1 | | 6/2018 | |
| WO | 2018107692 A1 | | 6/2018 | |
| WO | 2018107707 A1 | | 6/2018 | |
| WO | 2018108161 A1 | | 6/2018 | |
| WO | 2018/234861 A1 | | 12/2018 | |
| WO | 2019114839 A1 | | 6/2019 | |
| WO | 2021143906 A1 | | 7/2021 | |
| WO | 2021155867 A1 | | 8/2021 | |
| WO | 2021160092 A1 | | 8/2021 | |
| WO | 2021170099 A1 | | 9/2021 | |
| WO | 2021190558 A1 | | 9/2021 | |
| WO | 2021190561 A1 | | 9/2021 | |
| WO | 2021190562 A1 | | 9/2021 | |
| WO | 2021227417 A1 | | 11/2021 | |

OTHER PUBLICATIONS

International Preliminary Report on Patentability, issued Sep. 22, 2022, for PCT/CN2021/082725, filed Mar. 24, 2021, 5 pages. English Translation.

International Search Report and Written Opinion, mailed Jun. 29, 2021, for PCT/CN2021/082725, filed Mar. 24, 2021, 18 pages. English Translation.

NCBI Reference (Aug. 17, 2022). "NP000292.1—Plasminogen Isoform 1 Precursor [*Homo sapiens*]," 13 pages.

PDB: 1BUI (May 25, 2020). "Structure of the Ternary Microplasmin-Staphylokinase-Microplasmin Complex: A Proteinase-Cofactor-Substrate Complex in Action," Worldwide Protein Data Bank, 22 pages.

U.S. Appl. No. 17/914,271, filed Sep. 23, 2022, Li, Jinan (Copy not submitted herewith pursuant to the waiver of 37 C.F.R. 1.98(a)(2)(iii) issued by the Office on Sep. 21, 2004).

U.S. Appl. No. 18/022,084, filed Feb. 17, 2023, Li, Jinan (Copy not submitted herewith pursuant to the waiver of 37 C.F.R. 1.98(a)(2)(iii) issued by the Office on Sep. 21, 2004).

U.S. Appl. No. 18/037,300, filed May 16, 2023, Li, Jinan (Copy not submitted herewith pursuant to the waiver of 37 C. F.R. 1.98(a)(2)(iii) issued by the Office on Sep. 21, 2004).

Akassoglou, K. et al. (Apr. 27, 2004). "Fibrin Depletion Decreases Inflammation and Delays the Onset of Demyelination in a Tumor Necrosis Factor Transgenic Mouse Model for Multiple Sclerosis," Proceeding of the National Academy of Sciences 101(17):6698-6703.

Akassoglou, K. et al. (May 29, 2000). "Tissue Plasminogen Activator-Mediated Fibrinolysis Protects Against Axonal Degeneration and Demyelination After Sciatic Nerve Injury," The Journal of Cell Biology 149(5):1157-1166.

Angelucci, F. et al. (Mar. 1, 2019). "Amyloid Beta Soluble Forms and Plasminogen Activation System in Alzheimer's Disease: Consequences on Extracellular Maturation of Brain-Derived Neurotrophic Factor and Therapeutic Implications," CNS Neuroscience & Therapeutics 25(3):303-313.

Bahri, M. (2016). "Review: A Novel Multiple Sclerosis Model Utilizing Cuprizone and Rapamycin," PDXScholar, 32 pages.

Bruno, M.A. et al. (Apr. 25, 2006). "Activity-Dependent Release of Precursor Nerve Growth Factor, Conversion to Mature Nerve Growth Factor, and its Degradation by a Protease Cascade," Proceedings of the National Academy of Sciences 103(17):6735-6740.

Chen, N. et al. (2018). "Subacute Intranasal Administration of Tissue Plasm Inogen Activator Improves Stroke Recovery by Inducing Axonal Remodeling in Mice," Experimental Neurology 304:82-89.

Cops, E.J. et al. (Nov. 2013, e-pub. Aug. 9, 2013). "Tissue-Type Plasminogen Activator is an Extracellular Mediator of Purkinje Cell Damage and Altered Gait," Experimental Neurology 249:8-19.

Cuzner, M.L. et al. (1999). "Plasminogen Activators and Matrix Metalloproteases, Mediators of Extracellular Proteolysis in Inflammatory Demyelination of the Central Nervous System," Journal of Neuroimmunology 94:1-14.

Gudi, V. et al. (Mar. 13, 2014). "Glial Response During Cuprizone-Induced De- and Remyelination in the CNS: Lessons Learned," Frontiers in Cellular Neuroscience 8:73, 24 pages.

Kim, K.S. et al. (Mar. 22, 2012). "Proteolytic Cleavage of Extracellular a-Synuclein by Plasminu: Implications for Parkinson Disease," Journal of Biological Chemistry 287(30):24862-24872.

Kragyaur, M. et al. (Aug. 1, 2015). "Non-Viral Transfer of BDNF and uPA Stimulates Peripheral Nerve Regeneration," Biomedicine & Pharmacotherapy 74:63-70, 16 pages.

Melchor, J.P. et al. (Oct. 1, 2003). "The Tissue Plasminogen Activator-Plasminogen Proteolytic Cascade Accelerates Amyloid-β (Aβ) Degradation and Inhibits Aβ-Induced Neurodegeneration," The Journal of Neuroscience 23(26):8867-8871.

Mullins, E.S. et al. (Nov. 15, 2013). "Plasmin(ogen) Deficiency is Protective Against the Development of Neuroinflammatory Pathologies and Paralysis in a Murine Model of Multiple Sclerosis," Blood 122(21):1990, 2 pages.

NCBI Reference (Apr. 30, 2025). "NP000292.1—Plasminogen Isoform 1 Precursor [*Homo sapiens*],", 5 pages.

Park, S.M. et al. (Mar. 1, 2013, e-pub. Nov. 15, 2012). "Proteolytic Clearance of Extracellular a-Synuclein as a New Therapeutic Approach Against Parkinson Disease," Prion 7(2):121-126.

Pelisch, N. et al. (Apr. 27, 2015). "Plasminogen Activator Inhibitor-1 Antagonist TM5484 Attenuates Demyelination and Axonal Degeneration in an Mice Model of Multiple Sclerosis," PloS ONE 10(4):e0124510, 17 pages.

Pérez-Martìn, M.Y. et al. (2017). "Can Fibrinolytic System Components Explain Cognitive Impairment in Multiple Sclerosis?" Journal of the Neurological Sciences 382:66-72.

Xia, Y. et al. (Sep. 25, 2018). "Tissue Plasminogen Activator Promotes White Matter Integrity and Functional Recovery in a Murine Model of Traumatic Brain Injury," Proceedings of the National Academy of Sciences 115(39):E9230-E9238.

Yepes, M. (2019). "The Plasminogen Activation System Promotes Neurorepair in the Ischemic Brain," Current Drug Targets 20(9):953-995.

Zea. M.A. et al. (2010). "Relationship Between Fibrinolytic System and Neurological Disease," Rev. Neurol. 51:295-301. English Abstract, 8 pages.

* cited by examiner

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial sequence
<220> FEATURE:
<223> OTHER INFORMATION: nucleotide sequence of the natural plasminogen
      (Glu-PLG,Glu-plasminogen) without the signal peptide

<400> SEQUENCE: 1

gagcctctgg atgactatgt gaatacccag ggggcttcac tgttcagtgt cactaagaag     60

cagctgggag caggaagtat agaagaatgt gcagcaaaat gtgaggagga cgaagaattc    120

acctgcaggg cattccaata tcacagtaaa gagcaacaat gtgtgataat ggctgaaaac    180

aggaagtcct ccataatcat taggatgaga gatgtagttt tatttgaaaa gaaagtgtat    240

ctctcagagt gcaagactgg gaatggaaag aactacagag ggacgatgtc caaaacaaaa    300

aatggcatca cctgtcaaaa atggagttcc acttctcccc acagacctag attctcacct    360

gctacacacc cctcagaggg actggaggag aactactgca ggaatccaga caacgatccg    420

caggggccct ggtgctatac tactgatcca gaaaagagat atgactactg cgacattctt    480

gagtgtgaag aggaatgtat gcattgcagt ggagaaaact atgacggcaa aatttccaag    540

accatgtctg gactggaatg ccaggcctgg gactctcaga gcccacacgc tcatggatac    600

attccttcca aatttccaaa caagaacctg aagaagaatt actgtcgtaa ccccgatagg    660

gagctgcggc cttggtgttt caccaccgac cccaacaagc gctgggaact ttgtgacatc    720

ccccgctgca caacacctcc accatcttct ggtcccacct accagtgtct gaagggaaca    780

ggtgaaaact atcgcgggaa tgtggctgtt accgtgtccg ggcacacctg tcagcactgg    840

agtgcacaga cccctcacac acataacagg acaccagaaa acttcccctg caaaaatttg    900

gatgaaaact actgccgcaa tcctgacgga aaaagggccc catggtgcca tacaaccaac    960

agccaagtgc ggtgggagta ctgtaagata ccgtcctgtg actcctcccc agtatccacg   1020

gaacaattgg ctcccacagc accacctgag ctaacccctg tggtccagga ctgctaccat   1080

ggtgatggac agagctaccg aggcacatcc tccaccacca ccacaggaaa gaagtgtcag   1140

tcttggtcat ctatgacacc acaccggcac cagaagaccc cagaaaacta cccaaatgct   1200
```

```
ggcctgacaa tgaactactg caggaatcca gatgccgata aaggcccctg gtgttttacc   1260

acagacccca gcgtcaggtg ggagtactgc aacctgaaaa aatgctcagg aacagaagcg   1320

agtgttgtag cacctccgcc tgttgtcctg cttccagatg tagagactcc ttccgaagaa   1380

gactgtatgt ttgggaatgg gaaaggatac cgaggcaaga gggcgaccac tgttactggg   1440

acgccatgcc aggactgggc tgcccaggag ccccatagac acagcatttt cactccagag   1500

acaaatccac gggcgggtct ggaaaaaaat tactgccgta accctgatgg tgatgtaggt   1560

ggtccctggt gctacacgac aaatccaaga aaactttacg actactgtga tgtccctcag   1620

tgtgcggccc cttcatttga ttgtgggaag cctcaagtgg agccgaagaa atgtcctgga   1680

agggttgtag gggggtgtgt ggcccaccca cattcctggc cctggcaagt cagtcttaga   1740

acaaggtttg gaatgcactt ctgtggaggc accttgatat ccccagagtg ggtgttgact   1800

gctgcccact gcttggagaa gtccccaagg ccttcatcct acaaggtcat cctgggtgca   1860

caccaagaag tgaatctcga accgcatgtt caggaaatag aagtgtctag gctgttcttg   1920

gagcccacac gaaaagatat tgccttgcta aagctaagca gtcctgccgt catcactgac   1980

aaagtaatcc cagcttgtct gccatcccca aattatgtgg tcgctgaccg gaccgaatgt   2040

ttcatcactg gctggggaga aacccaaggt acttttggag ctggccttct caaggaagcc   2100

cagctccctg tgattgagaa taaagtgtgc aatcgctatg agtttctgaa tggaagagtc   2160

caatccaccg aactctgtgc tgggcatttg gccggaggca ctgacagttg ccagggtgac   2220

agtggaggtc ctctggtttg cttcgagaag gacaaataca ttttacaagg agtcacttct   2280

tggggtcttg gctgtgcacg ccccaataag cctggtgtct atgttcgtgt ttcaaggttt   2340

gttacttgga ttgagggagt gatgagaaat aattaa                             2376
```

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen (Glu-PLG,Glu-plasminogen) without the signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140
```

-continued

```
Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
```

```
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790


<210> SEQ ID NO 3
<211> LENGTH: 2433
<212> TYPE: DNA
<213> ORGANISM: Artificial sequence
<220> FEATURE:
<223> OTHER INFORMATION: nucleotide sequence of the natural plasminogen
      (from swiss prot) with the signal peptide

<400> SEQUENCE: 3

atggaacata aggaagtggt tcttctactt cttttatttc tgaaatcagg tcaaggagag     60

cctctggatg actatgtgaa tacccagggg gcttcactgt tcagtgtcac taagaagcag    120

ctgggagcag gaagtataga agaatgtgca gcaaaatgtg aggaggacga agaattcacc    180

tgcagggcat tccaatatca cagtaaagag caacaatgtg tgataatggc tgaaaacagg    240

aagtcctcca taatcattag gatgagagat gtagttttat ttgaaaagaa agtgtatctc    300

tcagagtgca agactgggaa tggaaagaac tacagaggga cgatgtccaa aacaaaaaat    360

ggcatcacct gtcaaaaatg gagttccact tctccccaca gacctagatt ctcacctgct    420

acacacccct cagagggact ggaggagaac tactgcagga atccagacaa cgatccgcag    480

gggccctggt gctatactac tgatccagaa aagagatatg actactgcga cattcttgag    540

tgtgaagagg aatgtatgca ttgcagtgga gaaaactatg acggcaaaat ttccaagacc    600

atgtctggac tggaatgcca ggcctgggac tctcagagcc cacacgctca tggatacatt    660

ccttccaaat ttccaaacaa gaacctgaag aagaattact gtcgtaaccc cgatagggag    720
```

-continued

```
ctgcggcctt ggtgtttcac caccgacccc aacaagcgct gggaactttg tgacatcccc    780

cgctgcacaa cacctccacc atcttctggt cccacctacc agtgtctgaa gggaacaggt    840

gaaaactatc gcgggaatgt ggctgttacc gtgtccgggc acacctgtca gcactggagt    900

gcacagaccc ctcacacaca taacaggaca ccagaaaact tcccctgcaa aaatttggat    960

gaaaactact gccgcaatcc tgacggaaaa agggccccat ggtgccatac aaccaacagc   1020

caagtgcggt gggagtactg taagataccg tcctgtgact cctccccagt atccacggaa   1080

caattggctc ccacagcacc acctgagcta acccctgtgg tccaggactg ctaccatggt   1140

gatggacaga gctaccgagg cacatcctcc accaccacca caggaaagaa gtgtcagtct   1200

tggtcatcta tgacaccaca ccggcaccag aagaccccag aaaactaccc aaatgctggc   1260

ctgacaatga actactgcag gaatccagat gccgataaag gcccctggtg ttttaccaca   1320

gaccccagcg tcaggtggga gtactgcaac ctgaaaaaat gctcaggaac agaagcgagt   1380

gttgtagcac ctccgcctgt tgtcctgctt ccagatgtag agactccttc cgaagaagac   1440

tgtatgtttg ggaatgggaa aggataccga ggcaagaggg cgaccactgt tactgggacg   1500

ccatgccagg actgggctgc ccaggagccc catagacaca gcattttcac tccagagaca   1560

aatccacggg cgggtctgga aaaaaattac tgccgtaacc ctgatggtga tgtaggtggt   1620

ccctggtgct acacgacaaa tccaagaaaa ctttacgact actgtgatgt ccctcagtgt   1680

gcggcccctt catttgattg tgggaagcct caagtggagc cgaagaaatg tcctggaagg   1740

gttgtagggg ggtgtgtggc ccacccacat tcctggccct ggcaagtcag tcttagaaca   1800

aggtttggaa tgcacttctg tggaggcacc ttgatatccc cagagtgggt gttgactgct   1860

gcccactgct tggagaagtc cccaaggcct tcatcctaca aggtcatcct gggtgcacac   1920

caagaagtga atctcgaacc gcatgttcag gaaatagaag tgtctaggct gttcttggag   1980

cccacacgaa aagatattgc cttgctaaag ctaagcagtc ctgccgtcat cactgacaaa   2040

gtaatcccag cttgtctgcc atccccaaat tatgtggtcg ctgaccggac cgaatgtttc   2100

atcactggct ggggagaaac ccaaggtact tttggagctg gccttctcaa ggaagcccag   2160

ctccctgtga ttgagaataa agtgtgcaat cgctatgagt ttctgaatgg aagagtccaa   2220

tccaccgaac tctgtgctgg gcatttggcc ggaggcactg acagttgcca gggtgacagt   2280

ggaggtcctc tggtttgctt cgagaaggac aaatacattt tacaaggagt cacttcttgg   2340

ggtcttggct gtgcacgccc caataagcct ggtgtctatg ttcgtgtttc aaggtttgtt   2400

acttggattg agggagtgat gagaaataat taa                                2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence of the natural plasminogen (from swiss prot) with the signal peptide

<400> SEQUENCE: 4

```
Met Glu His Lys Glu Val Val Leu Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
```

-continued

```
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460

Pro Pro Val Val Leu Leu Pro Asp Val Glu Thr Pro Ser Glu Glu Asp
465                 470                 475                 480
```

```
Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810
```

```
<210> SEQ ID NO 5
<211> LENGTH: 2145
<212> TYPE: DNA
<213> ORGANISM: Artificial sequence
<220> FEATURE:
<223> OTHER INFORMATION: nucleotide sequence of LYS77-PLG(Lys-
      plasminogen)

<400> SEQUENCE: 5

aaagtgtatc tctcagagtg caagactggg aatggaaaga actacagagg gacgatgtcc      60

aaaacaaaaa atggcatcac ctgtcaaaaa tggagttcca cttctcccca cagacctaga     120
```

```
ttctcacctg ctacacaccc ctcagaggga ctggaggaga actactgcag gaatccagac    180
aacgatccgc aggggccctg gtgctatact actgatccag aaaagagata tgactactgc    240
gacattcttg agtgtgaaga ggaatgtatg cattgcagtg gagaaaacta tgacggcaaa    300
atttccaaga ccatgtctgg actggaatgc caggcctggg actctcagag cccacacgct    360
catggataca ttccttccaa atttccaaac aagaacctga agaagaatta ctgtcgtaac    420
cccgataggg agctgcggcc ttggtgtttc accaccgacc ccaacaagcg ctgggaactt    480
tgtgacatcc cccgctgcac aacacctcca ccatcttctg gtcccaccta ccagtgtctg    540
aagggaacag gtgaaaacta tcgcgggaat gtggctgtta ccgtgtccgg gcacacctgt    600
cagcactgga gtgcacagac ccctcacaca cataacagga caccagaaaa cttcccctgc    660
aaaaatttgg atgaaaacta ctgccgcaat cctgacggaa aaagggcccc atggtgccat    720
acaaccaaca gccaagtgcg gtgggagtac tgtaagatac cgtcctgtga ctcctcccca    780
gtatccacgg aacaattggc tcccacagca ccacctgagc taacccctgt ggtccaggac    840
tgctaccatg gtgatggaca gagctaccga ggcacatcct ccaccaccac cacaggaaag    900
aagtgtcagt cttggtcatc tatgacacca caccggcacc agaagacccc agaaaactac    960
ccaaatgctg gcctgacaat gaactactgc aggaatccag atgccgataa aggcccctgg   1020
tgttttacca cagaccccag cgtcaggtgg gagtactgca acctgaaaaa atgctcagga   1080
acagaagcga gtgttgtagc acctccgcct gttgtcctgc ttccagatgt agagactcct   1140
tccgaagaag actgtatgtt tgggaatggg aaaggatacc gaggcaagag ggcgaccact   1200
gttactggga cgccatgcca ggactgggct gcccaggagc cccatagaca cagcattttc   1260
actccagaga caaatccacg ggcgggtctg gaaaaaaatt actgccgtaa ccctgatggt   1320
gatgtaggtg gtccctggtg ctacacgaca aatccaagaa aactttacga ctactgtgat   1380
gtccctcagt gtgcggcccc ttcatttgat tgtgggaagc ctcaagtgga gccgaagaaa   1440
tgtcctggaa gggttgtagg ggggtgtgtg gcccacccac attcctggcc ctggcaagtc   1500
agtcttagaa caaggtttgg aatgcacttc tgtggaggca ccttgatatc cccagagtgg   1560
gtgttgactg ctgcccactg cttggagaag tccccaaggc cttcatccta caaggtcatc   1620
ctgggtgcac accaagaagt gaatctcgaa ccgcatgttc aggaaataga agtgtctagg   1680
ctgttcttgg agcccacacg aaaagatatt gccttgctaa agctaagcag tcctgccgtc   1740
atcactgaca aagtaatccc agcttgtctg ccatccccaa attatgtggt cgctgaccgg   1800
accgaatgtt tcatcactgg ctggggagaa acccaaggta cttttggagc tggccttctc   1860
aaggaagccc agctccctgt gattgagaat aaagtgtgca atcgctatga gtttctgaat   1920
ggaagagtcc aatccaccga actctgtgct gggcatttgg ccggaggcac tgacagttgc   1980
cagggtgaca gtggaggtcc tctggtttgc ttcgagaagg acaaatacat tttacaagga   2040
gtcacttctt ggggtcttgg ctgtgcacgc cccaataagc ctggtgtcta tgttcgtgtt   2100
tcaaggtttg ttacttggat tgagggagtg atgagaaata attaa                   2145
```

<210> SEQ ID NO 6
<211> LENGTH: 714
<212> TYPE: PRT
<213> ORGANISM: Artificial sequence
<220> FEATURE:
<223> OTHER INFORMATION: amino acid sequence of LYS77-PLG(Lys-plasminogen)

<400> SEQUENCE: 6

-continued

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
```

```
            420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710


<210> SEQ ID NO 7
<211> LENGTH: 1245
<212> TYPE: DNA
<213> ORGANISM: Artificial sequence
<220> FEATURE:
<223> OTHER INFORMATION: nucleotide sequence of delta-plg(delta-
      plasminogen)

<400> SEQUENCE: 7

gagcctctgg atgactatgt gaatacccag ggggcttcac tgttcagtgt cactaagaag     60

cagctgggag caggaagtat agaagaatgt gcagcaaaat gtgaggagga cgaagaattc    120

acctgcaggg cattccaata tcacagtaaa gagcaacaat gtgtgataat ggctgaaaac    180

aggaagtcct ccataatcat taggatgaga gatgtagttt tatttgaaaa gaaagtgtat    240

ctctcagagt gcaagactgg gaatggaaag aactacagag ggacgatgtc caaaacaaaa    300

aatggcatca cctgtcaaaa atggagttcc acttctcccc acagacctag attctcacct    360
```

-continued

```
gctacacacc cctcagaggg actggaggag aactactgca ggaatccaga caacgatccg    420

caggggccct ggtgctatac tactgatcca gaaaagagat atgactactg cgacattctt    480

gagtgtgaag aggcggcccc ttcatttgat tgtgggaagc ctcaagtgga gccgaagaaa    540

tgtcctggaa gggttgtagg ggggtgtgtg gcccacccac attcctggcc ctggcaagtc    600

agtcttagaa caaggtttgg aatgcacttc tgtggaggca ccttgatatc cccagagtgg    660

gtgttgactg ctgcccactg cttggagaag tccccaaggc cttcatccta caaggtcatc    720

ctgggtgcac accaagaagt gaatctcgaa ccgcatgttc aggaaataga agtgtctagg    780

ctgttcttgg agcccacacg aaaagatatt gccttgctaa agctaagcag tcctgccgtc    840

atcactgaca aagtaatccc agcttgtctg ccatccccaa attatgtggt cgctgaccgg    900

accgaatgtt tcatcactgg ctggggagaa acccaaggta cttttggagc tggccttctc    960

aaggaagccc agctccctgt gattgagaat aaagtgtgca atcgctatga gtttctgaat   1020

ggaagagtcc aatccaccga actctgtgct gggcatttgg ccggaggcac tgacagttgc   1080

cagggtgaca gtggaggtcc tctggtttgc ttcgagaagg acaaatacat tttacaagga   1140

gtcacttctt ggggtcttgg ctgtgcacgc cccaataagc ctggtgtcta tgttcgtgtt   1200

tcaaggtttg ttacttggat tgagggagtg atgagaaata attaa                   1245
```

```
<210> SEQ ID NO 8
<211> LENGTH: 414
<212> TYPE: PRT
<213> ORGANISM: Artificial sequence
<220> FEATURE:
<223> OTHER INFORMATION: amino acid sequence of delta-plg(delta-
      plasminogen)

<400> SEQUENCE: 8

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205
```

```
His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
            340                 345                 350

Leu Ala Gly Gly Thr Asp Ser Cys Gln Gly Asp Ser Gly Gly Pro Leu
        355                 360                 365

Val Cys Phe Glu Lys Asp Lys Tyr Ile Leu Gln Gly Val Thr Ser Trp
    370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410
```

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence of Mini-plg(mini-plasminogen)

<400> SEQUENCE: 9

```
gtcaggtggg agtactgcaa cctgaaaaaa tgctcaggaa cagaagcgag tgttgtagca     60

cctccgcctg ttgtcctgct tccagatgta gagactcctt ccgaagaaga ctgtatgttt    120

gggaatggga aaggataccg aggcaagagg gcgaccactg ttactgggac gccatgccag    180

gactgggctg cccaggagcc ccatagacac agcattttca ctccagagac aaatccacgg    240

gcgggtctgg aaaaaaatta ctgccgtaac cctgatggtg atgtaggtgg tccctggtgc    300

tacacgacaa atccaagaaa actttacgac tactgtgatg tccctcagtg tgcggcccct    360

tcatttgatt gtgggaagcc tcaagtggag ccgaagaaat gtcctggaag ggttgtaggg    420

gggtgtgtgg cccacccaca ttcctggccc tggcaagtca gtcttagaac aaggtttgga    480

atgcacttct gtggaggcac cttgatatcc ccagagtggg tgttgactgc tgcccactgc    540

ttggagaagt ccccaaggcc ttcatcctac aaggtcatcc tgggtgcaca ccaagaagtg    600

aatctcgaac cgcatgttca ggaaatagaa gtgtctaggc tgttcttgga gcccacacga    660

aaagatattg ccttgctaaa gctaagcagt cctgccgtca tcactgacaa agtaatccca    720

gcttgtctgc catccccaaa ttatgtggtc gctgaccgga ccgaatgttt catcactggc    780

tggggagaaa cccaaggtac ttttggagct ggccttctca aggaagccca gctccctgtg    840
```

```
attgagaata aagtgtgcaa tcgctatgag tttctgaatg gaagagtcca atccaccgaa    900

ctctgtgctg ggcatttggc cggaggcact gacagttgcc agggtgacag tggaggtcct    960

ctggtttgct tcgagaagga caaatacatt ttacaaggag tcacttcttg ggtcttggc    1020

tgtgcacgcc ccaataagcc tggtgtctat gttcgtgttt caaggtttgt tacttggatt   1080

gagggagtga tgagaaataa ttaa                                          1104


<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-
      plasminogen)

<400> SEQUENCE: 10

Val Arg Trp Glu Tyr Cys Asn Leu Lys Lys Cys Ser Gly Thr Glu Ala
1               5                   10                  15

Ser Val Val Ala Pro Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
    130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205

Ile Glu Val Ser Arg Leu Phe Leu Glu Pro Thr Arg Lys Asp Ile Ala
    210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
    290                 295                 300

His Leu Ala Gly Gly Thr Asp Ser Cys Gln Gly Asp Ser Gly Gly Pro
```

```
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
        355                 360                 365


<210> SEQ ID NO 11
<211> LENGTH: 750
<212> TYPE: DNA
<213> ORGANISM: Artificial sequence
<220> FEATURE:
<223> OTHER INFORMATION: nucleotide sequence of Micro-plg(micro-
      plasminogen)

<400> SEQUENCE: 11

gccccttcat ttgattgtgg gaagcctcaa gtggagccga agaaatgtcc tggaagggtt      60

gtagggggggt gtgtggccca cccacattcc tggccctggc aagtcagtct tagaacaagg    120

tttggaatgc acttctgtgg aggcaccttg atatccccag agtgggtgtt gactgctgcc    180

cactgcttgg agaagtcccc aaggccttca tcctacaagg tcatcctggg tgcacaccaa    240

gaagtgaatc tcgaaccgca tgttcaggaa atagaagtgt ctaggctgtt cttggagccc    300

acacgaaaag atattgcctt gctaaagcta agcagtcctg ccgtcatcac tgacaaagta    360

atcccagctt gtctgccatc cccaaattat gtggtcgctg accggaccga atgtttcatc    420

actggctggg gagaaaccca aggtactttt ggagctggcc ttctcaagga agcccagctc    480

cctgtgattg agaataaagt gtgcaatcgc tatgagtttc tgaatggaag agtccaatcc    540

accgaactct gtgctgggca tttggccgga ggcactgaca gttgccaggg tgacagtgga    600

ggtcctctgg tttgcttcga gaaggacaaa tacattttac aaggagtcac ttcttggggt    660

cttggctgtg cacgccccaa taagcctggt gtctatgttc gtgtttcaag gtttgttact    720

tggattgagg gagtgatgag aaataattaa                                      750


<210> SEQ ID NO 12
<211> LENGTH: 249
<212> TYPE: PRT
<213> ORGANISM: Artificial sequence
<220> FEATURE:
<223> OTHER INFORMATION: amino acid sequence of Micro-plg(micro-
      plasminogen)

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110
```

```
Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245


<210> SEQ ID NO 13
<211> LENGTH: 684
<212> TYPE: DNA
<213> ORGANISM: Artificial sequence
<220> FEATURE:
<223> OTHER INFORMATION: nucleotide sequence of the serine protease
      domain

<400> SEQUENCE: 13

gttgtagggg ggtgtgtggc ccacccacat tcctggccct ggcaagtcag tcttagaaca     60

aggtttggaa tgcacttctg tggaggcacc ttgatatccc cagagtgggt gttgactgct    120

gcccactgct tggagaagtc cccaaggcct tcatcctaca aggtcatcct gggtgcacac    180

caagaagtga atctcgaacc gcatgttcag gaaatagaag tgtctaggct gttcttggag    240

cccacacgaa aagatattgc cttgctaaag ctaagcagtc ctgccgtcat cactgacaaa    300

gtaatcccag cttgtctgcc atccccaaat tatgtggtcg ctgaccggac cgaatgtttc    360

atcactggct ggggagaaac ccaaggtact tttggagctg gccttctcaa ggaagcccag    420

ctccctgtga ttgagaataa agtgtgcaat cgctatgagt ttctgaatgg aagagtccaa    480

tccaccgaac tctgtgctgg gcatttggcc ggaggcactg acagttgcca gggtgacagt    540

ggaggtcctc tggtttgctt cgagaaggac aaatacattt tacaaggagt cacttcttgg    600

ggtcttggct gtgcacgccc caataagcct ggtgtctatg ttcgtgtttc aaggtttgtt    660

acttggattg agggagtgat gaga                                           684


<210> SEQ ID NO 14
<211> LENGTH: 228
<212> TYPE: PRT
<213> ORGANISM: Artificial sequence
<220> FEATURE:
<223> OTHER INFORMATION: amino acid sequence of the serine protease
      domain

<400> SEQUENCE: 14

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30
```

-continued

```
Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225
```

METHOD AND MEDICINE FOR TREATING HUNTINGTON'S DISEASE

CROSS REFERENCE TO RELATED APPLICATIONS

This application is a national stage application under 35 U.S.C. § 371 of International Application No. PCT/CN2021/082725, filed Mar. 24, 2021, which claims priority to Chinese Application No. 202010213463.1, filed Mar. 24, 2020, the entire contents of each priority application are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922003000SEQLIST.TXT, date recorded: Sep. 22, 2022, size: 46,816 bytes).

FIELD OF THE INVENTION

The present invention relates to a method for treating Huntington's disease, which includes: administering an effective amount of a component of a plasminogen activation pathway or a related compound thereof, such as plasminogen, to a subject to treat Huntington's disease.

BACKGROUND OF THE INVENTION

Huntington's disease (HD), also known as chorea major or Huntington's chorea, is a neurodegenerative disease having autosomal dominant inheritance. Its pathogenic gene is the IT-15 gene (also called the HTT gene) located at chromosome 4p16.3, which has abnormal amplification of cytosine-adenine-guanine (CAG) trinucleotide repeats in patients with Huntington's disease and has complete penetrance when the number of copies is greater than 40. Patients usually develop the disease in middle age, with main symptoms including progressive movement disorders typically characterized by dance-like symptoms, cognitive decline, and psychiatric symptoms. At present, the second-generation antipsychotic drugs, such as tetrabenazine and olanzapine, are often used to control dance-like symptoms; and antidepressants are often used to improve psychiatric symptoms such as depression. However, these drugs do not slow down the progression of the disease. Currently, some studies are actively exploring the etiological treatment through gene therapy, but there are many uncertainties in gene therapy. Therefore, how to find more effective treatment methods in another way has become the focus of research on the disease.

SUMMARY OF THE INVENTION

The present invention finds that plasminogen can significantly improve Huntington's disease and its related symptoms, for example, can improve movement disorders of a subject with Huntington's disease, improve cognitive impairment, decelerate weight loss, protect undamaged neurons, promote the repair of damaged neurons and/or improve psychiatric symptoms, which provides an effective treatment method of Huntington's disease.

The present invention relates to the following items.

1. In an aspect, the present invention relates to a method for treating Huntington's disease, which includes: administering a therapeutically effective amount of one or more compounds to a subject with Huntington's disease. The one or more compounds are selected from: a component of a plasminogen activation pathway, a compound capable of directly activating plasminogen or indirectly activating plasminogen by activating an upstream component of a plasminogen activation pathway, a compound mimicking the activity of plasminogen or plasmin, a compound capable of up-regulating the expression of plasminogen or a plasminogen activator, a plasminogen analog, a plasmin analog, a tPA or uPA analog, and an antagonist of a fibrinolysis inhibitor.

In an aspect, the present invention relates to use of one or more compounds in preparation of a drug for treating Huntington's disease. The one or more compounds are selected from: a component of a plasminogen activation pathway, a compound capable of directly activating plasminogen or indirectly activating plasminogen by activating an upstream component of a plasminogen activation pathway, a compound mimicking the activity of plasminogen or plasmin, a compound capable of up-regulating the expression of plasminogen or a plasminogen activator, a plasminogen analog, a plasmin analog, a tPA or uPA analog, and an antagonist of a fibrinolysis inhibitor.

In an aspect, the present invention relates to a drug or pharmaceutical composition for treating Huntington's disease that contains one or more compounds. The one or more compounds are selected from: a component of a plasminogen activation pathway, a compound capable of directly activating plasminogen or indirectly activating plasminogen by activating an upstream component of a plasminogen activation pathway, a compound mimicking the activity of plasminogen or plasmin, a compound capable of up-regulating the expression of plasminogen or a plasminogen activator, a plasminogen analog, a plasmin analog, a tPA or uPA analog, and an antagonist of a fibrinolysis inhibitor.

2. The method, the use, the drug or the pharmaceutical composition according to item 1, wherein the component of the plasminogen activation pathway is selected from: plasminogen, recombinant human plasmin, Lys-plasminogen, Glu-plasminogen, plasmin, a plasminogen or plasmin variant or analog containing one or more Kringle domains or protease domains of plasminogen or plasmin, mini-plasminogen, mini-plasmin, micro-plasminogen, micro-plasmin, delta-plasminogen, delta-plasmin, a plasminogen activator, tPA, and uPA.

3. The method, the use, the drug or the pharmaceutical composition according to item 1, wherein the antagonist of the fibrinolysis inhibitor is an inhibitor of PAI-1, a complement C1 inhibitor, $\alpha 2$ antiplasmin or an $\alpha 2$ macroglobulin, such as an antibody.

4. The method, the use, the drug or the pharmaceutical composition according to any one of items 1 to 3, wherein the compound has one or more effects on the subject with Huntington's disease. The one or more effects are selected from: improvement or relief of movement disorders, improvement of cognitive impairment, deceleration of weight loss, promotion of the repair of damaged neurons, improvement of neuropsychiatric symptoms, relief of anxiety, reduction of the expression of GFAP in the hippocampus, reduction of apoptosis of hippocampal cells, promotion of the recovery of the number of Nissl bodies in cerebellar, hippocampal or striatal neurons, repair of damage to the hippocampus, striatum or olfactory tubercle, promotion of the expression of BDNF in the hippocampus or striatum, and promotion of the regeneration of striatal myelin sheaths.

5. The method, the use, the drug or the pharmaceutical composition according to any one of items 1 to 4, wherein the compound is used in combination with one or more other drugs or treatment method.

6. The method, the use, the drug or the pharmaceutical composition according to item 5, wherein the other drugs or treatment methods are selected from one or more of: anti-dopaminergic drugs, dopamine receptor inhibitors, antipsychotic drugs (e.g., butyrophenone and phenothiazines), γ-aminobutyrate transaminase inhibitors, cell transplantation therapy, and gene therapy.

7. The method, the use, the drug or the pharmaceutical composition according to any one of items 1 to 6, wherein the compound is plasminogen.

8. The method, the use, the drug or the pharmaceutical composition according to any one of items 1 to 7, wherein the plasminogen is human full-length plasminogen or a conservatively substituted variant.

9. The method, the use, the drug or the pharmaceutical composition according to any one of items 1 to 7, wherein the plasminogen has at least 75%, 80%, 85%, 90%, 95%, 96%, 97%, 98% or 99% sequence identity with sequence 2, and still has the lysine binding activity or the proteolytic activity of plasminogen.

10. The method, the use, the drug or the pharmaceutical composition according to any one of items 1 to 7, wherein the plasminogen is a protein containing an amino acid sequence having at least 80%, 90%, 95%, 96%, 97%, 98% or 99% amino acid sequence identity with sequence 14 and still having the proteolytic activity of plasminogen.

11. The method, the use, the drug or the pharmaceutical composition according to any one of items 1 to 7, wherein the plasminogen is selected from: Glu-plasminogen, Lys-plasminogen, mini-plasminogen, micro-plasminogen, delta-plasminogen, and variants thereof that retain the proteolytic activity of plasminogen.

12. The method, the use, the drug or the pharmaceutical composition according to any one of items 1 to 7, wherein the plasminogen contains an amino acid sequence shown as sequence 2, 6, 8, 10 or 12, or contains a conservatively substituted variant of the amino acid sequence shown as sequence 2, 6, 8, 10 or 12.

13. The method, the use, the drug or the pharmaceutical composition according to any one of items 1 to 12, wherein the compound is administered by nasal inhalation, aerosol inhalation, nasal drops, eye drops, ear drops, an intravenous method, an intraperitoneal method, a subcutaneous method, an intracranial method, an intrathecal method, an intra-arterial method (e.g., via the carotid artery) or an intramuscular method.

In any one of the above embodiments of the present invention, the plasminogen may have at least 75%, 80%, 85%, 90%, 95%, 96%, 97%, 98% or 99% sequence identity with sequence 2, 6, 8, 10 or 12, and still have the activity, such as the lysine binding activity and the proteolytic activity, of plasminogen. In some embodiments, the plasminogen is a protein that is obtained by adding, deleting and/or substituting 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid on the basis of sequence 2, 6, 8, 10 or 12, and still has the activity, such as the lysine binding activity and the proteolytic activity, of plasminogen.

In some embodiments, the plasminogen is a protein containing a plasminogen active fragment and still having the activity, such as the lysine binding activity and the proteolytic activity, of plasminogen. In some embodiments, the plasminogen is selected from Glu-plasminogen, Lys-plasminogen, mini-plasminogen, micro-plasminogen, delta-plasminogen, and variants thereof that retain the activity, such as the proteolytic activity, of plasminogen. In some embodiments, the plasminogen is natural or synthesized human plasminogen, or a variant or fragment thereof that retains the activity, such as the lysine binding activity and the proteolytic activity, of plasminogen. In some embodiments, the plasminogen is a human plasminogen ortholog from a primate or a rodent, or a variant or fragment thereof that retains the activity, such as the lysine binding activity and the proteolytic activity, of plasminogen. In some embodiments, the plasminogen has an amino acid sequence shown as sequence 2, 6, 8, 10 or 12. In some embodiments, the plasminogen is human natural plasminogen.

In some embodiments, the subject is a human. In some embodiments, the subject has the plasminogen deficiency. In some embodiments, the deficiency is congenital, secondary and/or local.

In some embodiments, the pharmaceutical composition contains a pharmaceutically acceptable carrier and plasminogen used in the above method. In some embodiments, the kit may be a preventive or therapeutic kit, which includes: (i) plasminogen used in the above method and a (ii) means for delivering the plasminogen to the subject. In some embodiments, the means is a syringe or a vial. In some embodiments, the kit also includes a label or instructions. The label or the instructions indicate that the plasminogen is administered to the subject to implement any one of the above methods.

In some embodiments, the product includes: a container with a label; and plasminogen used in the above method or a pharmaceutical composition containing plasminogen. The label indicates that the plasminogen or the composition is administered to the subject to implement any one of the above methods.

In some embodiments, the kit or the product also includes one or more other means or containers. The means or the containers contain other drugs.

In some embodiments of the above method, the plasminogen is administered systemically or locally, and preferably, the plasminogen is administered intravenously, intramuscularly or subcutaneously to the subject to treat the disease. In some embodiments of the above method, the plasminogen is administered in combination with a suitable polypeptide carrier or stabilizer. In some embodiments of the above method, the plasminogen is administered daily at a dose of 0.0001-2000 mg/kg, 0.001-800 mg/kg, 0.01-600 mg/kg, 0.1-400 mg/kg, 1-200 mg/kg, 1-100 mg/kg or 10-100 mg/kg (based on per kilogram of the body weight), or at a dose of 0.0001-2000 $mg/cm^2$, 0.001-800 $mg/cm^2$, 0.01-600 $mg/cm^2$, 0.1-400 $mg/cm^2$, 1-200 $mg/cm^2$, 1-100 $mg/cm^2$ or 10-100 $mg/cm^2$ (based on per square centimetre of the body surface area), preferably, administration is repeated at least once, and preferably, administration is performed at least daily.

The present invention explicitly covers all combinations of the technical features belonging to the embodiments of the present invention, and these combined technical solutions have been explicitly disclosed in this application, just as the above technical solutions have been separately and explicitly disclosed. In addition, the present invention also explicitly covers combinations of the embodiments and their elements, and the combined technical solutions are explicitly disclosed herein.

DETAILED DESCRIPTION OF THE INVENTION

Figure 1:
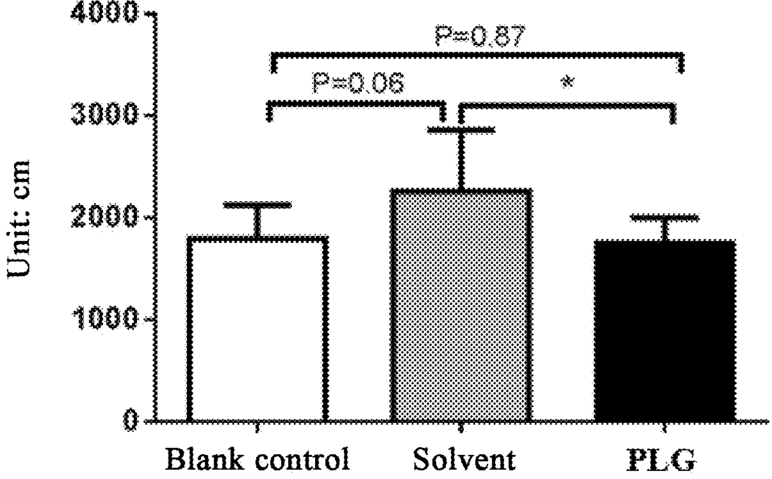
FIG. 1 shows statistical results of a total travel distance of a mouse model of Huntington's disease in an open field test after 7 days of plasminogen administration. The results show that a mouse of a blank control group travels a certain distance in the test; a total travel distance of a mouse of solvent control group is obviously longer than that of the mouse of the blank control group; a total travel distance of a mouse of a plasminogen administration group is obviously shorter than that of the mouse of the solvent control group, the statistical difference is significant (* indicates P<0.05), and the total travel distance of a mouse of the plasminogen administration group is closer to that of the mouse of the blank control group. It indicates that plasminogen can promote the recovery of spontaneous activities of the mouse model of Huntington's disease.

Huntington's disease (HD) is a monogenic neurodegenerative disease having autosomal dominant inheritance, its pathogenesis is dominated by mHtt protein toxicity, and its main symptoms include progressive movement disorders typically characterized by dance-like symptoms, cognitive decline, and psychiatric symptoms. When a gene mutation causes an abnormal increase in the number CAG copies, an amino-terminal (N-terminal) polyglutamine chain (polyQ) of a mutant Htt (mHtt) protein can be extended to form an abnormal conformation including a lamellar structure. As a result, the mHtt protein loses normal function and gains toxicity.

The "movement disorders" in Huntington's disease are mainly divided into two types, i.e., involuntary movement disorders (dominated by chorea) and voluntary movement disorders (including uncoordinated movements and slow movements). The progressive movement disorders are characterized by sudden and rapid throbbing or twitching of the limbs, face, or trunk that is unpredictable and uncontrollable, or characterized by uncontrollable slow movements. Dance-like involuntary movements and decreased muscle tone may be detected on examination. Dance-like involuntary movements are the most prominent features of the disease, mostly starting with brief uncontrollable grimacing, nodding, and finger flexion and extension movements, similar to painless convulsions, but slower and non-stereotyped. With the progression of the disease, involuntary movements progressively worsen, typical eyebrow raising and head flexion occur, patients turn the head when staring at objects and walk unsteadily with a leaping gait and constantly changing hand posture, and the whole body moves like dance. In the later stage of the disease, patient cannot stand and walk due to involuntary movements of the whole body. With the progression of the disease, the impairment of voluntary movements becomes more pronounced, with clumsiness, slowness, and rigidity in movements, inability to maintain complex voluntary movements, dysphagia, hesitate in speech, and dysarthria. Abnormal eye movements occur. In the advanced stage of the disease, the limbs may be in a stuporous state, that is, the limbs cannot move.

The dance-like movement disorder is the typical feature of adult-onset Huntington's disease. In juvenile patients with onset before the age of 20, immobile myotonia is the main movement disorder, manifesting as myotonia, myoclonus, and opisthotonus in the later stage. In addition, differing from adult patients, about 50% of juvenile patients with Huntington's disease has the onset of systematic epilepsy.

The "cognitive impairment" in Huntington's disease can appear years before motor symptoms, and its progression is relatively slow. Progressive dementia is another feature of patients with Huntington's disease. Dementia is characterized by subcortical dementia in the early stage and characterized by mixed cortical and subcortical dementia in the later stage.

The cognitive impairment can appear in the early stage of Huntington's disease. At the beginning, patient show a decline in memory and computing abilities in daily life and work, with only mild impairments in remembering new information, but significant deficits in recall. The patients show changes in speech function, including oral disfluency, mild difficulty in finding words, and dysarthria. Impaired oral fluency is one of the earliest cognitive impairments in Huntington's disease. In the middle stage and advanced stage of the disease, patients are unable to complete a naming test that requires recall of infrequent words. Dance-like movement disorders often affect the tongue and lips to disrupt the rhythm and agility of pronunciation and interfere with the volume, speed, rhythm, and length of phrases of speech. Therefore, dysarthria and rhythm disorders are prominent features of patients with this disease.

The "neuropsychiatric symptoms" of Huntington's disease may appear very early, and may even be the first symptoms, such as depression, irritability, and apathy, while more severe symptoms include paranoia or schizophrenia-like symptoms Fibrinolytic system is a system composed of a series of chemical substances involved in fibrinolysis. The chemical substances mainly include plasminogen, plasmin, plasminogen activators, and fibrinolysis inhibitors. The plasminogen activators include a tissue-type plasminogen activator (t-PA) and a urokinase-type plasminogen activator (u-PA). t-PA is a serine protease synthesized by vascular endothelial cells. t-PA activates plasminogen mainly on fibrin. The urokinase-type plasminogen activator (u-PA) is produced by renal tubular epithelial cells and vascular endothelial cells, and can directly activate plasminogen without the need for fibrin as a cofactor. Plasminogen (PLG) is synthesized in the liver. When blood coagulates, a large amount of PLG is adsorbed onto the fibrin network, and is activated to plasmin under the action of t-PA or u-PA to promote fibrinolysis. Plasmin (PL) is a serine protease, and has the following effects: degrading fibrin and fibrinogen; hydrolyzing a variety of blood coagulation factors such as V, VIII, X, VII, XI, and II; enabling plasminogen to be transformed into plasmin; hydrolyzing complements, etc. The fibrinolysis inhibitors include: plasminogen activator inhibitors (PAIs) and α2 antiplasmin (α2-AP). PAIs mainly include two types, i.e., PAI-1 and PAI-2, and can specifically bind to t-PA in a ratio of 1:1 to inactivate t-PA and activate PLG at the same time. α2-AP is synthesized in the liver, and binds to PL in a ratio of 1:1 to form a complex so as to inhibit the activity of PL. FXIII enables α2-AP to bind to fibrin in the form of covalent bond to attenuate the sensitivity of fibrin to the action of PL. Substances inhibiting the activity of the fibrinolytic system in vivo include: PAI-1, a complement C1 inhibitor, α2 antiplasmin, and an α2 macroglobulin.

Herein, the term "component of a plasminogen activation pathway" covers:

1. plasminogen, Lys-plasminogen, Glu-plasminogen, micro-plasminogen, delta-plasminogen, and variants and analogs thereof;
2. plasmin and variants and analogs thereof; and
3. plasminogen activators, such as tPA, uPA, and a tPA or uPA variant or analog containing one or more domains (e.g., one or more Kringle domains and proteolysis domains) of tPA or uPA.

The above "variants" of plasminogen, plasmin, tPA, and uPA include all naturally occurring human genetic variants and other mammalian forms of these proteins, and a protein that is obtained by adding, deleting and/or substituting, for example, 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid and still has the activity of plasminogen, plasmin, tPA or uPA. For example, the "variants" of plasminogen, plasmin, tPA, and uPA include mutational variants of these proteins that are obtained by substituting, for example, 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid with conservative amino acids.

The "plasminogen variants" of the present invention include proteins having at least 75%, 80%, 85%, 90%, 95%, 96%, 97%, 98% or 99% sequence identity with sequence 2, 6, 8, 10 or 12 and still having the activity, such as the lysine binding activity and the proteolytic activity, of plasminogen. For example, the "plasminogen variants" of the present invention may be proteins that are obtained by adding, deleting and/or substituting 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid on the basis of sequence 2, 6, 8, 10 or 12 and still have the activity, such as the lysine binding activity and the proteolytic activity, of plasminogen. Specifically, the plasminogen variants of the present invention include all naturally occurring human genetic variants and other mammalian forms of these proteins, and mutational variants of these proteins that are obtained by substituting, for example, 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid with conservative amino acids.

The plasminogen of the present invention may be a human plasminogen ortholog from a primate or a rodent, or a variant thereof that retains the activity, such as the lysine binding activity and the proteolytic activity, of plasminogen, such as plasminogen shown as sequence 2, 6, 8, 10 or 12, and human natural plasminogen shown as sequence 2.

The above "analogs" of plasminogen, plasmin, tPA, and uPA include compounds respectively providing functions basically similar to those of plasminogen, plasmin, tPA, or uPA.

The above "variants" and "analogs" of plasminogen, plasmin, tPA, and uPA include "variants" and "analogs" containing one or more domains (e.g., one or more Kringle domains and proteolysis domains) of plasminogen, plasmin, tPA, and uPA. For example, the "variants" and "analogs" of plasminogen include plasminogen variants and analogs containing one or more domains (e.g., one or more Kringle domains and proteolysis domains) of plasminogen, such as mini-plasminogen. The "variants" and "analogs" of plasmin include plasmin "variants" and "analogs" containing one or more domains (e.g., one or more Kringle domains and proteolysis domains) of plasmin, such as mini-plasmin and delta-plasmin (δ-plasmin).

Whether the above "variants" or "analogs" of plasminogen, plasmin, tPA or uPA have the activity of plasminogen, plasmin, tPA or uPA, or whether the above "variants" or "analogs" of plasminogen, plasmin, tPA or uPA respectively provides functions basically similar to those of plasminogen, plasmin, tPA or uPA can be detected by the methods known in the art. For example, the activity of activated plasmin is determined by enzymography, an enzyme-linked immunosorbent assay (ELISA) or fluorescence-activated cell sorting (FACS), or determined by the methods described in the following documents: Ny, A., Leonardsson, G., Hagglund, A. C, Hagglof, P., Ploplis, V. A., Carmeliet, P. and Ny, T. (1999). Ovulation inplasminogen-deficient mice. Endocrinology 140, 5030-5035; Silverstein R L, Leung L L, Harpel P C, Nachman R L (November 1984). "Complex formation of platelet thrombospondin with plasminogen. Modulation of activation by tissue activator". J. Clin. Invest. 74 (5): 1625-33; Gravanis I, Tsirka S E (February 2008). "Tissue-type plasminogen activator as a therapeutic target in stroke". Expert Opinion on Therapeutic Targets. 12 (2): 159-70; and Geiger M, Huber K, Wojta J, Stingl L, Espana F, Griffin J H, Binder B R (August 1989). "Complex formation between urokinase and plasma protein C inhibitor in vitro and in vivo". Blood. 74 (2): 722-8.

In some embodiments of the present invention, the "component of the plasminogen activation pathway" of the present invention is plasminogen. In some embodiments, the plasminogen is human full-length plasminogen or a conservatively substituted variant thereof that retains the activity (e.g., the lysine binding activity and the proteolytic activity) of plasminogen. In some embodiments, the plasminogen is selected from Glu-plasminogen, Lys-plasminogen, mini-plasminogen, micro-plasminogen, delta-plasminogen, and variants thereof that retain the activity (e.g., the lysine binding activity and the proteolytic activity) of plasminogen. In some embodiments, the plasminogen is natural or synthesized human plasminogen, or a conservatively substituted variant or fragment thereof that retains the activity (e.g., the lysine binding activity and the proteolytic activity) of plasminogen. In some embodiments, the plasminogen is a human plasminogen ortholog from a primate or a rodent, or a conservatively substituted variant or fragment thereof that retains the activity of plasminogen. In some embodiments, the plasminogen contains an amino acid sequence shown as sequence 2, 6, 8, 10 or 12. In some embodiments, the plasminogen contains a conservatively substituted sequence of the amino acid sequence shown as sequence 2, 6, 8, 10 or 12. In some embodiments, the plasminogen has an amino acid sequence shown as sequence 2, 6, 8, 10 or 12. In some embodiments, the plasminogen is a conservatively substituted variant of plasminogen shown as sequence 2, 6, 8, 10 or 12. In some embodiments, the plasminogen is human natural plasminogen or a conservative mutant thereof. In some embodiments, the plasminogen is human natural plasminogen shown as sequence 2 or a conservatively substituted variant thereof.

A "compound capable of directly activating plasminogen or indirectly activating plasminogen by activating an upstream component of a plasminogen activation pathway" refers to any compound that can directly activate plasminogen or indirectly activate plasminogen by activating an upstream component of a plasminogen activation pathway, such as tPA, uPA, streptokinase, saruplase, alteplase, reteplase, tenecteplase, anistreplase, monteplase, lanoteplase, pamiteplase, and staphylokinase.

An "antagonist of a fibrinolysis inhibitor" of the present invention is a compound that antagonizes, weakens, blocks, or prevents the action of a fibrinolysis inhibitor. The fibrinolysis inhibitor is, for example, PAI-1, a complement C1 inhibitor, α2 antiplasmin or an α2 macroglobulin. The antagonist is, for example, an antibody of PAI-1, a complement C1 inhibitor, α2 antiplasmin or an α2 macroglobulin, or antisense RNA or small RNA that blocks or downregulates the expression of PAI-1, a complement C1 inhibitor, α2 antiplasmin or an α2 macroglobulin, or a compound that occupies a binding site of PAI-1, a complement C1 inhibitor, α2 antiplasmin or an α2 macroglobulin and does not have functions of PAI-1, a complement C1 inhibitor, α2 antiplasmin or an α2 macroglobulin, or compound that blocks a binding domain and/or an activity domain of PAI-1, a complement C1 inhibitor, α2 antiplasmin or an α2 macroglobulin.

Plasmin is a key component of a plasminogen activation (PA) system. It is a broad-spectrum protease, and can hydrolyze several components, including fibrin, gelatin, fibronectin, laminin, and proteoglycans, of an extracellular matrix (ECM). In addition, plasmin can activate some matrix metalloproteinase precursors (pro-MMPs) to activate matrix metalloproteinases (MMPs). Therefore, plasmin is considered as an important upstream regulator of extracellular proteolysis. Plasmin is formed by proteolysis of plasminogen with two types of physiological PAs, i.e., a tissue-type plasminogen activator (tPA) and a urokinase-type plasminogen activator (uPA). Due to relatively high levels of plasminogen in plasma and other body fluids, it has traditionally been thought that the regulation of the PA system is mainly achieved through the synthesis and activity levels of PAs. The synthesis of components of the PA system is strictly regulated by different factors, such as a hormone, a growth factor, and a cytokine. In addition, there are specific physiological inhibitors of plasmin and PAs. A main inhibitor of plasmin is α2-antiplasmin. The activity of PAs is regulated by both of a plasminogen activator inhibitor 1 (PAI-1) for inhibiting uPA and tPA and a plasminogen activator inhibitor 2 (PAI-2) for mainly inhibiting uPA. There are uPA-specific cell surface receptors (uPARs) having the direct hydrolysis activity on the surface of some cells.

Plasminogen is a single-stranded glycoprotein, is composed of 791 amino acids, and has a molecular wight of about 92 kDa. Plasminogen is mainly synthesized in the liver, and is abundant in the extracellular fluid. The plasminogen content in plasma is about 2 μM. Therefore, plasminogen is a huge potential source of the proteolytic activity in tissues and body fluids. Plasminogen is present in two molecular forms, i.e., glutamate-plasminogen (Glu-plasminogen) and lysine-plasminogen (Lys-plasminogen). Naturally secreted and uncleaved plasminogen has an amino-terminal (N-terminal) glutamate, so it is referred to as glutamate-plasminogen. However, glutamate-plasminogen is hydrolyzed to lysine-plasminogen at Lys76-Lys77 in the presence of plasmin Compared with glutamate-plasminogen, lysine-plasminogen has higher affinity to fibrin and can be activated by PAs at a higher rate. Arg560-Va1561 peptide bonds of the two forms of plasminogen can be cleaved by uPA or tPA to form double-stranded protease plasmin linked via a disulfide bond. The amino-terminal moiety of plasminogen contains five homologous tri-circles, i.e., kringles; and the carboxyl-terminal moiety of plasminogen contains protease domains. Some kringles contain lysine binding sites for mediating specific interaction of plasminogen and fibrin, as well as its inhibitor α2-AP. It is found recently that a plasminogen fragment of 38 kDa that contains Kringle1 to Kringle4 is an effective inhibitor for angiogenesis. This fragment is named angiostatin, which can be produced by hydrolyzing plasminogen with several proteases.

A main substrate of plasmin is fibrin, and the dissolution of fibrin is a key for preventing pathological thrombosis. Plasmin also has substrate specificity to several components, including laminin, fibronectin, proteoglycans, and gelatin, of ECM, suggesting that plasmin also plays an important role in reconstruction of ECM. Indirectly, plasmin can also degrade other components, including MMP-1, MMP-2, MMP-3, and MMP-9, of ECM by transforming some protease precursors into active proteases. Therefore, it has been proposed that plasmin may be an important upstream regulator of extracellular proteolysis. In addition, plasmin has the ability to activate certain potential growth factors. In vitro, plasmin can also hydrolyze components of a complement system and release chemotactic complement fragments.

"Plasmin" is a very important enzyme present in the blood, which can hydrolyze a fibrin clot to fibrin degradation products and D-dimer.

"Plasminogen" is the zymogen form of plasmin According to sequences in Swiss Prot, a glycoprotein composed 810 amino acids, having a molecular weight of about 90 kDa, mainly synthesized in the liver, and capable of circulating in the blood is calculated based on an amino acid sequence (sequence 4) of natural human plasminogen containing a signal peptide, and a cDNA sequence for encoding the amino acid sequence is shown as sequence 3. Full-length plasminogen contains seven domains, i.e., a serine protease domain at the C terminus, a Pan Apple (PAp) domain at the N terminus, and five Kringle domains (Kringle1 to Kringle5). Referring to sequences in Swiss Prot, the signal peptide includes residues Met1-Gly19, PAp includes residues Glu20-Va198, Kringle1 includes residues Cys103-Cys181, Kringle2 includes residues Glu184-Cys262, Kringle3 includes residues Cys275-Cys352, Kringle4 includes residues Cys377-Cys454, and Kringle5 includes residues Cys481-Cys560. According to data of NCBI, the serine protease domain includes residues Va1581-Arg804.

Glu-plasminogen is human natural full-length plasminogen and is composed of 791 amino acids (without a signal peptide of 19 amino acids), a cDNA sequence for encoding the sequence is shown as sequence 1, and an amino acid sequence of Glu-plasminogen is shown as sequence 2. In vivo, there is Lys-plasminogen formed by hydrolyzing Glu-plasminogen at amino acids at the 76th site and the 77th site, which is shown as sequence 6, and a cDNA sequence for encoding the amino acid sequence is shown as sequence 5. Delta-plasminogen (δ-plasminogen) is full-length plasminogen lacking a fragment from Kringle2 to Kringle5 and containing only Kringle1 and a serine protease domain (also referred to as a protease domain (PD)), an amino acid sequence (sequence 8) of delta-plasminogen has been reported in a document, and a cDNA sequence for encoding the amino acid sequence is shown as sequence 7. Mini-plasminogen is composed of Kringle5 and a serine protease domain, it has been reported in a document that an amino acid sequence of mini-plasminogen includes residues Va1443-Asn791 (taking a Glu residue in a sequence of Glu-plasminogen without a signal peptide as the starting amino acid), and is shown as sequence 10, and a cDNA sequence for encoding the amino acid sequence is shown as sequence 9. Micro-plasminogen contains only a serine protease domain, it has been reported in a document that an amino acid sequence of micro-plasminogen includes residues Ala543-Asn791 (taking a Glu residue in a sequence of Glu-plasminogen without a signal peptide as the starting amino acid), and it has also been reported in the patent document CN102154253A that the sequence of micro-plasminogen includes residues Lys531-Asn791 (taking a Glu residue in a sequence of Glu-plasminogen without a signal peptide as the starting amino acid). In this patent application, the amino acid sequence of micro-plasminogen is referred to the patent document CN102154253A, and is shown as sequence 12, and a cDNA sequence for encoding the amino acid sequence is shown as sequence 11.

The structure of full-length plasminogen is also described in the paper of Aisina, et al. (Aisina R B, Mukhametova L I. Structure and function of plasminogen/plasmin system W. Russian Journal of Bioorganic Chemistry, 2014, 40 (6): 590-605). In this paper, Aisina, et al. describe that plasminogen includes Kringle1, 2, 3, 4, and 5 domains and a serine protease domain (also referred to as a protease domain (PD)). Kringles are responsible for binding plasminogen to ligands having low molecular weights and high molecular weights (i.e., the lysine binding activity), so that plasminogen is transformed into a more open conformation, which can be activated more easily. The protease domain (PD) includes residues Va1562-Asn791, and tPA and uPA specifically cleave an activation bond at sites Arg561-Va1562 in plasminogen to transform plasminogen into plasmin Therefore, the protease domain (PD) is a region giving the proteolytic activity of plasminogen. Herein, the terms "plasmin", "fibrinolysin", and "fibrinolytic enzyme" are interchangeable and have the same meaning. The terms "plasminogen", "profibrinolysin", and "fibrinolytic zymogen" are interchangeable and have the same meaning.

In the present invention, the "plasminogen deficiency" means that the plasminogen content or activity in a subject is less than that in a normal person, and is low enough to affect normal physiological functions of the subject. The "plasminogen deficiency" means that the plasminogen content or activity in a subject is less than that in a normal person, the activity or expression of plasminogen is extremely low, and normal physiological functions can only be maintained by providing exogenous plasminogen.

Those in the art may understand that all technical solutions of plasminogen of the present invention are applicable to plasmin, and thus the technical solutions described in the present invention cover plasminogen and plasmin During circulation, plasminogen is in a closed inactive conformation, and is transformed into activate plasmin in an open conformation under the mediation of a plasminogen activator (PA) when binding to a thrombus or cell surface. Active plasmin can further hydrolyze a fibrin clot to fibrin degradation products and D-dimer, so as to dissolve a thrombus. The PAp domain of plasminogen contains an important determinant for maintaining plasminogen in a closed inactive conformation, and the KR domain of plasminogen can bind to a lysine residue present in a receptor and a substrate. A variety of known enzymes that can be used as plasminogen activators include: a tissue-type plasminogen activator (tPA), a urokinase-type plasminogen activator (uPA), a kallikrein, a blood coagulation factor XII (Hageman factor), etc.

A "plasminogen active fragment" refers to a fragment having the activity of binding to lysine in a target sequence of a substrate (the lysine binding activity), or the activity of exerting proteolytic function (the proteolytic activity), or the proteolytic activity and the lysine binding activity. The technical solutions related to plasminogen of the present invention cover a technical solution of replacing plasminogen with a plasminogen active fragment. In some embodiments, the plasminogen active fragment of the present invention contains the serine protease domain of plasminogen or is composed of the serine protease domain of plasminogen. In some embodiments, the plasminogen active fragment of the present invention contains sequence 14, or contains an amino acid sequence having at least 80%, 90%, 95%, 96%, 97%, 98% or 99% identity with sequence 14, or is composed of sequence 14, or is composed of the amino acid sequence having at least 80%, 90%, 95%, 96%, 97%, 98% or 99% identity with sequence 14. In some embodiments, the plasminogen active fragment of the present invention contains one or more regions selected from Kringle1, Kringle2, Kringle3, Kringle4, and Kringle5 or conservatively substituted variants thereof, or is composed of one or more regions selected from Kringle1, Kringle2, Kringle3, Kringle4, and Kringle5 or conservatively substituted variants thereof. In some embodiments, the plasminogen of the present invention includes a protein containing the above plasminogen active fragment.

At present, assays of plasminogen in the blood and its activity include: an tissue-type plasminogen activator activity assay (t-PAA), a plasma tissue-type plasminogen activator antigen assay (t-PAAg), a plasma tissue-type plasminogen activity assay (plgA), a plasma tissue plasminogen antigen assay (plgAg), a plasma tissue-type plasminogen activator inhibitor activity assay, a plasma tissue-type plasminogen activator inhibitor antigen assay, and a plasma plasmin-antiplasmin complex assay (PAP). The most commonly used test method is a chromogenic substrate method: streptokinase (SK) and a chromogenic substrate are added to plasma to be tested, PLG in the plasma to be tested is transformed into PLM under the action of SK, PLM acts on the chromogenic substrate, absorbance is measured by using a spectrophotometer, and increase in absorbance is proportional to the activity of plasminogen. In addition, immunohistochemistry, gel electrophoresis, immunoturbidimetry, radial immunodiffusion, etc. can also be adopted to test the activity of plasminogen in the blood.

An "ortholog" refers to a homolog of different species, includes a protein homolog and a DNA homolog, and is also referred to as a vertical homolog. It specifically refers to a protein or a gene in different species that has evolved from the same ancestral gene. The plasminogen of the present invention includes human natural plasminogen, and also includes plasminogen orthologs derived from different species and having the activity of plasminogen.

A "conservatively substituted variant" refers to that a given amino acid residue is changed, but the whole conformation and function of a protein or enzyme are not changed. For example, an amino acid in an amino acid sequence of a parent protein is substituted with an amino acid with similar properties (e.g., acidity, alkalinity, and hydrophobicity). The amino acid with similar properties is well known. For example, arginine, histidine, and lysine are hydrophilic alkaline amino acids and can be substituted with each other. Similarly, isoleucine is a hydrophobic amino acid and can be substituted with leucine, methionine or valine. Therefore, the similarity of amino acid sequences of two proteins having similar functions may be different. For example, 70% to 99% similarity (identity) based on the MEGALIGN algorithm. The "conservatively substituted variant" also includes a polypeptide or an enzyme that has more than 60% amino acid sequence identity determined based on BLAST or FASTA algorithm, preferably, more than 75% identity, more preferably, more than 85% identity, and the most preferably, more than 90% identity. The polypeptide or the enzyme has the same or basically similar properties or function compared to a natural or parent protein or enzyme.

"Isolated" plasminogen refers to a plasminogen protein isolated and/or recovered from a natural environment of plasminogen. In some embodiments, the plasminogen is purified (1) to the purity (by weight) of more than 90%, more than 95% or more than 98%, such as more than 99% determined by the Lowry method, (2) to an extent sufficient to obtain at least 15 residues at the N terminus or in an internal amino acid sequence by using a rotary cup sequencer, or (3) to homogeneity that is determined by sodium dodecyl sulfate-polyacrylamide gel electrophoresis (SDS-PAGE) using Coomassie blue or silver staining under reducing or non-reducing conditions. The isolated plasminogen also includes plasminogen prepared from a recombinant cell by a bioengineering technology and isolated by at least one purification step.

Herein, the terms "polypeptide", "peptide", and "protein" are interchangeable, refer to an aggregation form of amino acids of any length, and may include genetically encoded and non-genetically encoded amino acids, chemically or biogeochemically modified or derived amino acids, and a polypeptide having a modified peptide backbone. The terms include fusion proteins, which include, but are not limited to, a fusion protein having an heterogenous amino acid sequence, a fusion having heterogenous and homologous leader sequences (having or without an N-terminal methionine residue), etc.

"Amino acid sequence identity percentage (%)" relative to a reference polypeptide sequence is defined as, after gaps have been introduced as necessary to achieve the maximum percentage sequence identity, and no conservative substitutions are considered as a part of the sequence identity, the percentage of amino acid residues, which are identical to amino acid residues in the reference polypeptide sequence, in a candidate sequence. Comparison for determining percentage amino acid sequence identity can be achieved in a variety of ways within the technical scope of the art. For example, software available to the public, such as BLAST, BLAST-2, ALIGN, and Megalign (DNASTAR), is adopted. Those skilled in the art can determine appropriate parameters used for comparing sequences, such as any algorithm needed to achieve the maximum comparison over the full lengths of sequences to be compared. However, for the purpose of the present invention, an amino acid sequence identity percentage value is generated by using the sequence comparison computer program ALIGN-2.

In a case that ALIGN-2 is adopted to compare amino acid sequences, % amino acid sequence identity of a given amino acid sequence A relative to a given amino acid sequence B (or may be expressed as that the given amino acid sequence A has or contains certain % amino acid sequence identity relative to, with, or to the given amino acid sequence B) is calculated as follows:

$$X/Y \times 100\%$$

where, X is the number of amino acid residues, identically matched with amino acid residues in B, in A that is determined by the sequence comparison program ALIGN-2, and Y is the total number of amino acid residues in B. It is to be understood that in a case that the length of the amino acid sequence A differs from that of the amino acid sequence B, % amino acid sequence identity of A relative to B is not equal to % amino acid sequence identity of B relative to A. Unless otherwise specifically described, all % amino acid sequence identity values used herein are obtained by using the ALIGN-2 computer program as described in the preceding paragraph.

As used herein, the term "treatment" refers to obtaining a desired pharmacological and/or physiological effect. The effect may be complete or partial prevention of occurrence and onset of a disease or its symptoms, partial or complete alleviation of a disease and/or its symptoms, and/or partial or complete cure of a disease and/or its symptoms, which includes: (a) prevention of occurrence or onset of a disease in a subject who may have a predisposition to the disease but has not been diagnosed with the disease; (b) inhibition of a disease, i.e., retardation of the formation of the disease; and (c) alleviation of a disease and/or its symptoms, i.e. subsidence or disappearance of the disease and/or its symptoms.

Herein, the terms "individual", "subject", and "patient" are interchangeable, and refer to a mammal, which includes, but is not limited to, murine (rats and mice), non-human primates, humans, dogs, cats, ungulates (e.g., horses, cattle, sheep, pigs, and goats), etc.

A "therapeutically effective amount" or "effective dose" refers to an amount of a component of a plasminogen activation pathway or its related compound (e.g., plasminogen) that is sufficient to prevent and/or treat a disease when administered to a mammal or other subjects to treat the disease. The "therapeutically effective amount" is changed with the component of the plasminogen activation pathway or its related compound (e.g., plasminogen) used, a disease of a subject to be treated and/or the severity of symptoms, age, and weight, etc.

Preparation of the Plasminogen of the Present Invention

Plasminogen can be isolated from nature and purified for further therapeutic use, or can be synthesized by a standard chemical peptide synthesis technology. In a case that a polypeptide is synthesized chemically, plasminogen can be synthesized from a liquid phase or a solid phase. Solid-phase polypeptide synthesis (SPPS) (in which a C-terminal amino acid of a sequence is attached to an insoluble support, followed by sequential addition of the remaining amino acids in the sequence) is a method suitable for chemical synthesis of plasminogen. Various SPPS methods, such as Fmoc and Boc, can be used to synthesize plasminogen. The solid-phase synthesis technique is described in Barany, et al. Solid-Phase Peptide Synthesis; The Peptides: Analysis, Synthesis, Biology. Vol. 2: Special Methods in Peptide Synthesis, Part A, 3-284; Merrifield. Solid Phase Peptide Synthesis. I. The Synthesis of a Tetrapeptide. J. Am. Chem. Soc., 85: 2149-2156 (1963); Stewart, et al. Solid Phase Peptide Synthesis, 2nd ed. Pierce Chem. Co., Rockford, Ill. (1984); Ganesan A. 2006 Mini Rev. Med Chem. 6: 3-10; and Camarero J A, et al. 2005 Protein Pept Lett. 12: 723-8. In short, small insoluble porous beads are treated with a functional unit on which a peptide chain is built. After recirculation of coupling/deprotection, the attached solid-phase free N-terminal amine is coupled to a single N-protected amino acid unit. This unit is then deprotected to reveal a new N-terminal amine that can be attached to another amino acid. The peptide remains immobilized on the solid phase and then is cleaved.

The plasminogen of the present invention can be produced by a standard recombination method. For example, a nucleic acid for encoding plasminogen is inserted into an expression vector so as to be operably connected to a regulatory sequence in the expression vector. The expression regulatory sequence includes, but is not limited to, a promoter (e.g., a naturally related or heterogenous promoter), a signal sequence, an enhancer element, and a transcription termination sequence. The expression regulatory sequence may be a eukaryotic promoter system in the vector, and the vector can transform or transfect eukaryotic host cells (e.g., COS or CHO cells). Once the vector is incorporated into a suitable host, the vector maintains the host under conditions suitable for high expression of a nucleotide sequence and collection and purification of plasminogen.

The suitable expression vector usually replicates in the host organism as an episome or an integrated part of the host chromosomal DNA. Normally, the expression vector contains a selectable marker (e.g., ampicillin resistance, hygromycin resistance, tetracycline resistance, kanamycin resistance, and neomycin resistance) to facilitate detection of cells transformed with an exogenous desired DNA sequence.

Exemplary prokaryotic host cells that can be used to clone a polynucleotide for encoding a subject antibody include *Escherichia coli*. Other suitable microbial hosts include: *Bacillus* such as *Bacillus subtilis*, and other Enterobacteriaceae such as *Salmonella, Serratia*, and various *Pseudomonas* species. Expression vectors can also be generated in these prokaryotic hosts, and usually contain expression control sequences (origin of replication) compatible with the host cells. In addition, there are many known promoters, such as a lactose promoter system, a tryptophan (trp) promoter system, a beta-lactamase promoter system, and a promoter system from bacteriophage λ. The promoter usually controls expression optionally in a sequence of an operator gene, and has a ribosome binding site sequence for initiating and completing transcription and translation.

Other microorganisms, such as yeast, can also be used for expression. Exemplary suitable yeast host cells include yeast (e.g., *Saccharomyces cerevisiae* (*S. cerevisiae*)) and *Pichia*, and the suitable vector has an expression control sequence (e.g., a promoter), origin of replication, a terminator sequence, etc. according to the requirements. Typical promoters contain 3-phosphoglycerate kinase and other glycogenolysis enzymes. Inducible yeast promoters specially include promotes from alcohol dehydrogenase, hetero-cytochrome C, and enzymes responsible for using maltose and galactose.

In addition to microorganisms, mammalian cells (e.g., mammalian cells cultured in a cell culture medium in vitro) can also be used for expressing and generating the anti-Tau antibody (e.g., a polynucleotide for encoding a subject anti-Tau antibody) of the present invention. Referring to Winnacker, From Genes to Clones, VCH Publishers, N.Y., N.Y. (1987). Suitable mammal host cells include a CHO cell line, various Cos cell line, HeLa cells, a myeloma cell line, and transformed B cells or hybridoma. An expression vector used for these cells may include an expression control sequence such as origin of replication, a promoter, and an enhancer (Queen, et al. Immunol. Rev. 89: 49 (1986)), and a necessary information processing site such as a ribosome binding site, an RNA splicing site, a polyadenylation site, and a transcription terminator sequence. Exemplary suitable expression control sequences include derived promoters such as a white immunoglobulin gene, SV40, an adenovirus, a bovine papillomavirus, and a cytomegalovirus. Referring to Co, et al. J. Immunol. 148: 1149 (1992).

Once the plasminogen of the present invention is synthesized (by the chemical or recombination method), the plasminogen of the present invention is purified in accordance with the standard procedure in the art, which includes ammonium sulfate precipitation, affinity column, column chromatography, high performance liquid chromatography (HPLC), gel electrophoresis, etc. The plasminogen is substantially pure, for example, at least about 80% to 85% pure, at least 85% to 90% pure, at least about 90% to 95% pure, 98% to 99% pure or purer. For example, the plasminogen does not contain contaminants such as cellular debris and macromolecules other than the target product.

Drug Preparation

A therapeutic preparation is a lyophilized preparation or an aqueous solution formed by mixing plasminogen with required purity with an optional pharmaceutical carrier, excipient or stabilizer (Remington's Pharmaceutical Sciences, 16th edition, Osol, A. ed. (1980)). The acceptable carrier, excipient or stabilizer at a used dose and concentration is nontoxic to subjects, and includes a buffer such as phosphates, citrates, and other organic acids; an antioxidant such as ascorbic acid and methionine; a preservative (e.g., octadecyl dimethyl benzyl ammonium chloride, hexanediamine chloride, benzalkonium chloride, benzethonium chloride, phenol, butanol, benzyl alcohol, alkyl parabens such as methyl and ethyl parabens, catechol, resorcinol, cyclohexanol, 3-pentanol, and m-cresol); a polypeptide with a low molecular weight (less than about 10 residues); a protein such as serum albumin, gelatin, and immunoglobulin; a hydrophilic polymer such as polyvinylpyrrolidone; an amino acid such as glycine, glutamine, asparagine, histidine, arginine, and lysine; monosaccharide, disaccharide, and other carbohydrates such as glucose, mannose, and dextrin; a chelant such as EDTA; saccharides such as sucrose, mannitol, fucose, and sorbitol; salt-forming counterions such as sodium; a metal complex (e.g., a zinc-protein complex); and/or a non-ionic surfactant such as TWEEN™, PLURONICS™, and polyethylene glycol (PEG). A preferred lyophilized anti-VEGF antibody preparation is described in WO 97/04801, which is incorporated herein by reference.

The preparation of the present invention may also contain more than one active compound needed for treating a specific symptom, and preferably, the active compounds are complementary and do not have side effects on each other. For example, antihypertensive drugs, antiarrhythmic drugs, and drugs for treating diabetes.

The plasminogen of the present invention can be encapsulated in a microcapsule prepared by techniques such as coacervation or interfacial polymerization, for example, can be placed in a colloidal drug delivery system (e.g., a liposome, an albumin microsphere, a microemulsion, nanoparticles, and a nanocapsule) or placed in hydroxymethylcellulose in a macroemulsion or a gel-microcapsule and a poly-(methyl methacrylate) microcapsule. These techniques are disclosed in Remington's Pharmaceutical Sciences 16th edition, Osol, A. Ed. (1980).

The plasminogen of the present invention that is used for in vivo administration needs to be sterile. It can be easily achieved by filtration with a sterile filter before or after lyophilization and re-preparation.

The plasminogen of the present invention can be used in preparation of a sustained-release preparation. Exemplary suitable sustained-release preparations include semipermeable matrices of solid hydrophobic polymers having a shape and containing glycoproteins, such as membranes or microcapsules. Exemplary sustained-release matrices include polyesters, hydrogels (e.g., poly(2-hydroxyethyl-methacrylate) (Langer, et al. J. Biomed. Mater. Res., 15: 167-277 (1981); Langer, Chem. Tech., 12: 98-105 (1982)) or polyvinyl alcohol, polylactide (U.S. Pat. No. 3,773,919, EP 58,481), L-glutamic acid, and a γ ethyl-L-glutamic acid copolymer (Sidman, et al. Biopolymers 22: 547 (1983)), non-degradable ethylene-vinyl acetate (Langer, et al. same as above) or degradable lactic acid-glycolic acid copolymer such as Lupron Depot™ (an injectable microsphere composed of a lactic acid-glycolic acid copolymer and leuprolide acetate), and poly-D-(−)-3-hydroxybutyric acid. The copolymers, such as ethylene-vinyl acetate and lactic acid-glycolic acid, can sustainably release molecules for more than 100 days, and some hydrogels release proteins for a short time period. Rational strategies for stabilizing proteins can be designed based on the relevant mechanisms. For example, in a case that the mechanism of coacervation is formation of intermolecular S—S bonds through the exchange of thiodisulfide bonds, proteins can be stabilized by modifying sulfhydryl residues, lyophilizing from an acid solution, controlling humidity, using an appropriate additive, and developing a specific polymer matrix composition.

Administration and Dosage

The pharmaceutical composition of the present invention can be administered by different methods, such as nasal inhalation, aerosol inhalation, nasal drops or eye drops, an intravenous method, an intraperitoneal method, a subcutaneous method, an intracranial method, an intrathecal method, an intraarterial method (e.g., via the carotid artery), an intramuscular method, and a rectal administration.

Preparations for parenteral administration include sterile aqueous or non-aqueous solutions, suspensions, and emulsions. Non-aqueous solvents include propylene glycol, polyethylene glycol, vegetable oils such as olive oil, and injectable organic esters such as ethyl oleate. Aqueous vectors include water, alcoholic/aqueous solutions, emulsions, and suspensions such as saline and a buffer medium. Parenteral *intermedia* include a sodium chloride solution, Ringer's dextrose, dextrose, sodium chloride, and fixed oils. Intravenous *intermedia* include fluids and nutritional supplements, electrolyte supplements, etc. A preservative and other additives, such as an antimicrobial, an antioxidant, a chelator, and inert gas, may be present.

Medical staffs will determine a dosage regimen based on various clinical factors. As well known in the medical field, a dosage regimen for any patient is determined according to a variety of factors, including the body size of a patient, the body surface area, age, a specific compound to be administered, sex, the frequency and path of administration, general health conditions, and other drugs to be administered together. A daily dosage range of the pharmaceutical composition containing plasminogen of the present invention may be, for example, about 0.0001-2000 mg/kg, or about 0.001-500 mg/kg (e.g., 0.02 mg/kg, 0.25 mg/kg, 0.5 mg/kg, 0.75 mg/kg, 10 mg/kg, and 50 mg/kg) of body weight of a patient. For example, a dose may be 1 mg/kg of body weight or 50 mg/kg of body weight, or within a range of 1-50 mg/kg of body weight, or at least 1 mg/kg of body weight. Doses greater or less than these exemplary ranges are also covered, especially in view of the above factors. Intermediate doses within the above ranges also fall within the scope of the present invention. Subjects may be administered with the pharmaceutical composition at such doses daily, every other day, weekly, or according to any other regimen determined by empirical analysis. Exemplary dosage regimens include that the pharmaceutical composition is administered at 0.01-100 mg/kg for consecutive days. It is necessary to assess a therapeutic effect and the safety during administration with the drug of the present invention.

Product or Kit

An embodiment of the present invention relates to a product or kit, which includes the plasminogen or plasmin of the present invention that is used to treat cardiovascular diseases caused by diabetes and related symptoms thereof. Preferably, the product includes a container with a label or package insert. Suitable containers include bottles, vials, syringes, etc. The container can be made from a variety of materials such as glass and plastic. The container contains a composition that can be used to treat the disease or symptoms of the present invention, and has a sterile inlet (e.g. the container may be an intravenous solution pack or vial with a plug that can be penetrated by a hypodermic needle). At least one active ingredient in the composition is plasminogen/plasmin. The label attached to the container is used to describe that the composition is used to treat the cardiovascular diseases caused by diabetes and related symptoms thereof of the present invention. The product may also include a second container containing a medicinal buffer such as phosphate-buffered saline, a Ringer's solution, and a dextrose solution. The product may also include other substances required from a commercial and user standpoint, which include other buffers, a diluent, a filter, a needle, and a syringe. In addition, the product includes a package insert with instructions for use, which are used to, for example, indicate a user of the composition to administer the plasminogen composition and other drugs for treating concomitant diseases to a patient.

EXAMPLES

Human plasminogen used in all the following examples was from plasma of a human donator, that is, was isolated from plasma of a human donator and purified by a method optimized with reference to the methods described in the following documents: Kenneth C Robbins, Louis Summaria, David Elwyn, et al. Further Studies on the Purification and Characterization of Human Plasminogen and Plasmin Journal of Biological Chemistry, 1965, 240 (1): 541-550; Summaria L, Spitz F, Arzadon L, et al. Isolation and characterization of the affinity chromatography forms of human Glu- and Lys-plasminogens and plasmins J Biol Chem. 1976 Jun. 25; 251 (12): 3693-9; HAGAN JJ, ABLONDI FB, DE RENZO EC. Purification and biochemical properties of human plasminogen. J Biol Chem. 1960 April; 235: 1005-10. The purity of plasminogen monomers was greater than 98%.

Example 1 Plasminogen Improves Spontaneous Activities and Approach-Avoidance Behaviors of a Mouse Model of Huntington's Disease 3 days before model construction, 6-week-old male C57 mice were weighed and subjected to a simply open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mice of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were divided into two groups, i.e., a solvent control group (9 mice) and a plasminogen administration group (8 mice), according to total travel distances of the mice of the model group in the open field test. A solvent (a 10 mM sodium citrate solution, pH=7.4) was injected into each mouse of the solvent control group via the tail vein at a dose of 0.1 mL/day, human plasminogen was injected into each mouse of the plasminogen administration group via the tail vein at a dose of 1 mg/0.1 mL/day [v1], and administration was performed for 7 consecutive days. An open field test was performed on day 7 of administration.

3-NP is a natural mycotoxin, which can irreversibly inhibit mitochondrial succinate dehydrogenase, cross the blood-brain barrier to cause neurotoxicity, cause neuronal death, and mimic human HD symptoms[1].

Open Field Test

In the test, the mouse was placed in the central of the bottom of the open field (40×40×40 cm) while video recording and timing were performed at the same time. The mouse was continuously observed for 5 min, and 3 tests were performed on each mouse. The Smart system is a complete and user-friendly video tracking system for assessing behaviors of an experimental animal. It records trajectories, activities, specific behaviors (e.g., rotation, stretching, and feeding), and events, and calculates various analysis parameter. The test used the Smart3.0 system to record and analyze motions of the mice, and parameters included a total travel distance, a boundary zone resting time rate, a central zone average movement speed, and a boundary zone average movement speed. In each test, the box was wiped with 70% ethanol to prevent the preference caused by odor[1].

The open field test is designed based on the phobotaxis of mice, which means that mice are afraid of open, unknown, and potentially dangerous places, and thus have a natural tendency to move "against the wall". The phobotaxis is assessed based on activities of the mouse in surrounding zones (four corners and four sides) of the open field. In view of duration in the surrounding zones that reflects the phobotaxis, if the duration is shorter, the mouse is more "adventurous". If the duration in the central zone is longer, the phobotaxis and the anxiety (depression) level are lower.

Total Travel Distance

A total travel distance refers to the length of motion trails within the specified test time. The results show that in the test, the mouse of the blank control group travels a certain distance; a total travel distance of the mouse of the solvent control group is obviously longer than that of the mouse of the blank control group; a total travel distance of the mouse of the plasminogen administration group is obviously shorter than that of the mouse of the solvent control group, the statistical difference is significant (* indicates P<0.05), and the total travel distance of the mouse of the plasminogen administration group is close to that of the mouse of the blank control group (see FIG. 1). It indicates that plasminogen can promote the recovery of spontaneous activities of the mouse model of Huntington's disease.

Boundary Zone Resting Time Rate

Figure 2:
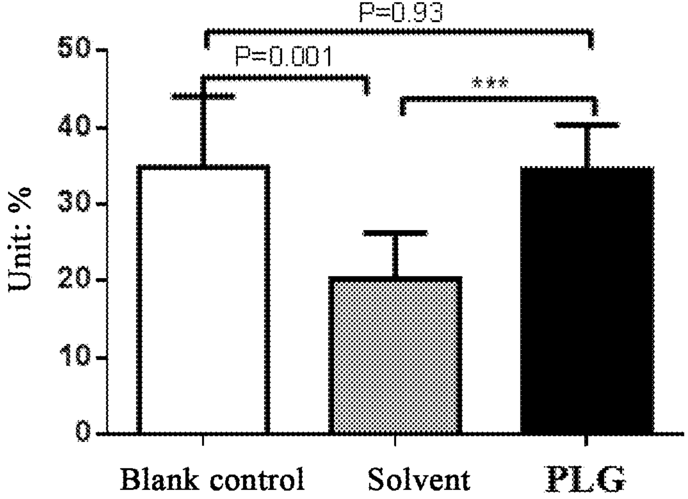
FIG. 2 shows statistical results of a boundary zone resting time rate of a mouse model of Huntington's disease in an open field test after 7 days of plasminogen administration. The results show that a mouse of a blank control group has a certain boundary zone resting time rate; a boundary zone resting time rate of a mouse of a solvent control group is obviously less than that of the mouse of the blank control group; a boundary zone resting time rate of a mouse of a plasminogen administration group is obviously greater than that of the mouse of the solvent control group, the statistical difference is extremely significant (*** indicates P<0.001), and the boundary zone resting time rate of the mouse of the plasminogen administration group is close to that of the mouse of the blank control group. It indicates that plasminogen can relieve anxiety behaviors of the mouse model of Huntington's disease.

Boundary zones are surrounding zones (for corners and four sides) of the open field. A boundary zone resting time rate refers to a ratio of boundary zone resting time to total resting time (including boundary zone resting time and central zone resting time). The results show that the mouse of the blank control group has a certain boundary zone resting time rate; a boundary zone resting time rate of the mouse of the solvent control group is obviously less than that of the mouse of the blank control group; a boundary zone resting time rate of the mouse of the plasminogen administration group is obviously greater than that of the mouse of the solvent control group, the statistical difference is extremely significant (* indicates P<0.001), and the boundary zone resting time rate of the mouse of the plasminogen administration group is close to that of the mouse of the blank control group (see FIG. 2**). It indicates that plasminogen can relieve anxiety behaviors of the mouse model of Huntington's disease.

Central Zone Average Movement Speed

Figure 3:
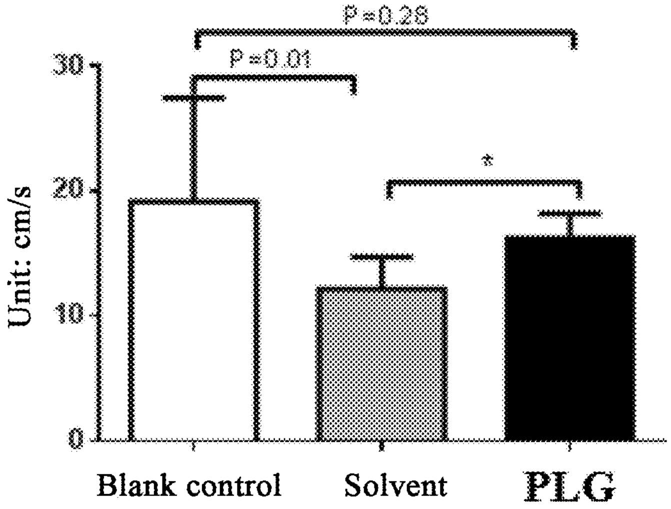
FIG. 3 shows statistical results of a central zone average movement speed of a mouse model of Huntington's disease in an open field test after 7 days of plasminogen administration. The results show that a mouse of a blank control group has a certain central zone movement speed; a central zone average movement speed of a mouse of a solvent control group is obviously lower than that of the mouse of the blank control group; a central zone average movement speed of a mouse of a plasminogen administration group is obviously higher than that of the mouse of the solvent control group, the statistical difference is significant (* indicates P<0.05), and the central zone movement speed of the mouse of the plasminogen administration group is close to that of the mouse of the blank control group. It indicates that plasminogen can promote the recovery of spontaneous activities and approach-avoidance behaviors and the relief of anxiety behaviors of the mouse model of Huntington's disease.

A central zone refers to a zone (20×20 cm) in the centre of the open field. A central zone average movement speed refers to a ratio of a central zone travel distance to total central zone duration (including travelling and resting time). The results show that the mouse of the blank control group has a certain central zone movement speed; a central zone average movement speed of the mouse of the solvent control group is obviously lower than that of the mouse of the blank control group; a central zone average movement speed of the mouse of the plasminogen administration group is obviously higher than that of the mouse of the solvent control group, the statistical difference is significant (* indicates P<0.05), and the central zone average movement speed of the mouse of the plasminogen administration group is close to that of the mouse of the blank control group (see FIG. 3). It indicates that plasminogen can promote spontaneous activities and relieve anxiety behaviors of the mouse model of Huntington's disease.

Boundary Zone Average Movement Speed

Figure 4:
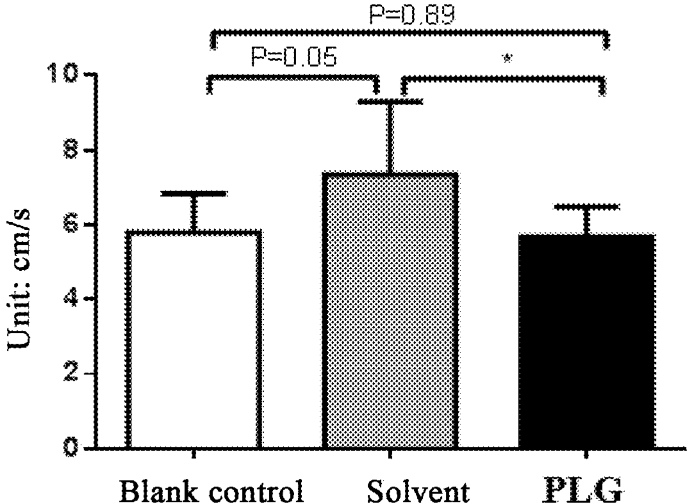
FIG. 4 shows statistical results of a boundary zone average movement speed of a mouse model of Huntington's disease in an open field test after 7 days of plasminogen administration. The results show that a mouse of a blank control group has a certain boundary zone movement speed; a boundary zone average movement speed of a mouse of a solvent control group is obviously higher than that of the blank control group; a boundary zone average movement speed of a mouse of a plasminogen administration group is obviously lower than that of the solvent control group, the statistical difference is significant (* indicates P<0.05), and the boundary zone average movement speed of the mouse of the plasminogen administration group is close to that of the mouse of the blank control group. It indicates that plasminogen can promote the recovery of spontaneous activities and approach-avoidance behaviors and the relief of anxiety behaviors of the mouse model of Huntington's disease.

A boundary zone average movement speed refers to a ratio of a total boundary zone travel distance to total boundary zone duration. The results show that the mouse of the blank control group has a certain boundary zone movement speed; a boundary zone average movement speed of the mouse of the solvent control group is obviously higher than that of the mouse of the blank control group; a boundary zone average movement speed of the mouse of the plasminogen administration group is obviously lower than that of the mouse of the solvent control group, the statistical difference is significant (* indicates P<0.05), and the boundary zone average movement speed of the mouse of the plasminogen administration group is close to that of the mouse of the blank control group (see FIG. 4). It indicates that plasminogen can promote spontaneous activities and relieve anxiety behaviors of the mouse model of Huntington's disease.

Motion Trail

Figure 5:
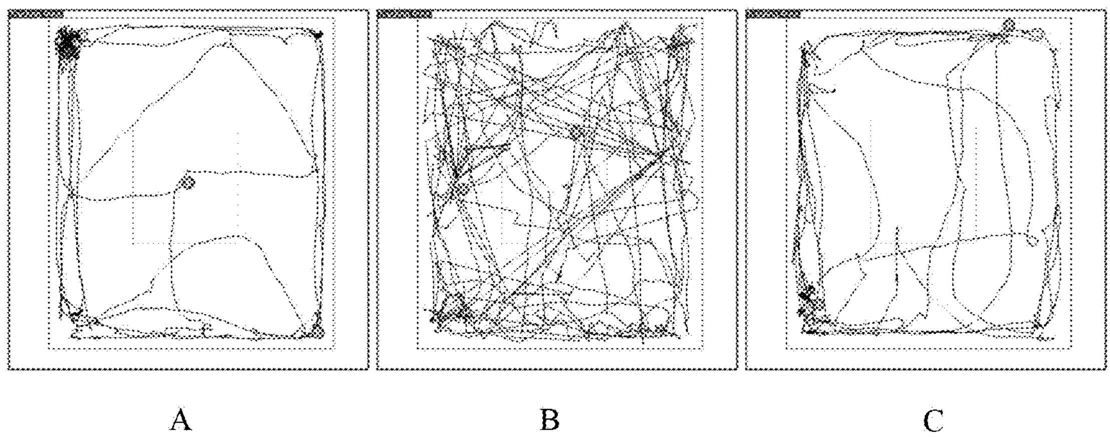
FIG. 5A to FIG. 5C are diagrams of motion trails of mouse models of Huntington's disease in an open field test after 7 days of plasminogen administration. A shows a blank control group, B shows a solvent control group, and C shows a plasminogen administration group. The results show that a mouse of the blank control group travels in a central zone less frequently and travels in a boundary zone more frequently, with regular motion trails; compared with the mouse of the blank control group, a mouse of the solvent group travels more frequently in the central zone and has an obviously increased total travel distance, with chaotic and irregular motion trails; a mouse of the plasminogen administration group travels less frequently in the central zone and has an obviously reduced total travel distance compared with the mouse of the solvent group, with motion trails similar to those of the mouse of the blank control group. It indicates that plasminogen can promote the recovery of spontaneous activities and approach-avoidance behaviors of the mouse model of Huntington's disease.

The results show that the mouse of the blank control group (see FIG. 5A) travels in the central zone less frequently and travels in the boundary zone more frequently, with regular motion trails; compared with the mouse of the blank control group, the mouse of the solvent group (see FIG. 5B) travels more frequently in the central zone and has an obviously increased total travel distance, with chaotic and irregular motion trails; the mouse of the plasminogen administration group (see FIG. 5C) travels less frequently in the central zone and has an obviously reduced total travel distance compared with the mouse of the solvent group, with motion trails similar to those of the mouse of the blank control group. It indicates that plasminogen can promote the recovery of spontaneous activities and approach-avoidance behaviors of the mouse model of Huntington's disease.

Example 2 Plasminogen Decelerates Weight Loss in a Mouse Model of Huntington's Disease 3 days before model construction, 6-week-old male C57 mice were weighed and subjected to a simple open field test.

The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were weighed on day 7 of administration, and the body weight percentage of each mouse was calculated on day 7 and day 0.

Weight loss is a common non-neural phenotype of Huntington's disease that is usually progressive and can lead to malnutrition or cachexia[5].

Figure 6:
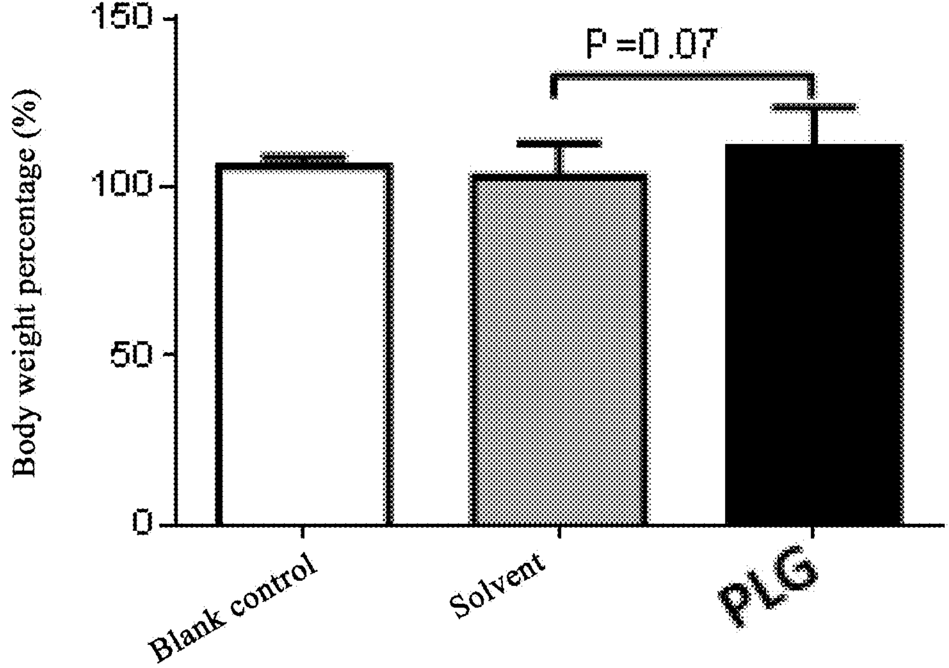
FIG. 6 shows calculation results of the body weight percentage of a mouse model of Huntington's disease on day 7 and day 0 after 7 days of plasminogen administration. The results show that the body weight percentage of a mouse of a blank control group is greater than 1, and the body weight tends to increase; the body weight percentage of a mouse of a solvent control group is less than that of the mouse of the blank control group; the body weight percentage of a mouse of a plasminogen administration group is obviously greater than that of the mouse of the solvent control group, and the statistical difference is close to significant (P=0.07). The results indicate that plasminogen can promote weight gain in the mouse model of Huntington's disease.

The results show that the body weight percentage of the mouse of the blank control group is greater than 1, and the body weight tends to increase; the body weight percentage of the mouse of the solvent control group is less than that of the mouse of the blank control group; the body weight percentage of the mouse of the plasminogen administration group is obviously greater than that of the mouse of the solvent control group, and the statistical difference is close to significant (P=0.07). (FIG. 6) The results indicate that plasminogen can promote weight gain in the mouse model of Huntington's disease.

Example 3 Plasminogen Reduces the Expression of GFAP in the Hippocampus of a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (10 mM citric acid-sodium citrate, pH=7.4) was injected into each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, the hippocampus was taken out and fixed in a 10% formaldehyde solution for 24-48 h. The fixed hippocampus tissue was dehydrated with graded ethanol, cleared with xylene, and embedded in paraffin. The tissue was cut into slices with a thickness of 3 μm, and the slice was subjected to deparaffinage and rehydration, and washed once with water. The tissue slice was marked by using a PAP pen, incubated in 3% hydrogen peroxide for 15 min, and washed twice with 0.01 M PBS for 5 min each time. The slice was blocked with a 5% normal goat serum (Vector laboratories, Inc., USA) for 30 min; and then, the goat serum was removed, a rabbit anti-GFAP antibody (Abcam, ab7260) was added dropwise, and the slice was incubated at 4° C. overnight and washed twice with 0.01 M PBS for 5 min each time. A goat anti-rabbit IgG (HRP) antibody (Abcam) secondary antibody was added, and the slice was incubated at the room temperature for 1 h and washed twice with 0.01 M PBS for 5 min each time. The slice was developed by using a DAB kit (Vector laboratories, Inc., USA), washed three times with water, restained with hematoxylin for 30 s, and rinsed with running water for 5 min. The stained slice was dehydrated with graded ethanol, cleared with xylene, sealed by a neutral gum, and observed under a 400× optical microscope.

Glial fibrillary acidic protein (GFAP) is a typical intermediate filament protein in an astrocyte, which is involved in the formation of a cytoskeleton and maintenance of the strength of the cytoskeleton. Astrocytes are one of main glial cells in the central nervous system, and studies have revealed that Huntington's disease is accompanied with the proliferation of astrocytes and improvement of the activity of astrocytes, which are characterized by up-regulation of the expression of GFAP and cellular hypertrophy[6-7].

Figure 7:
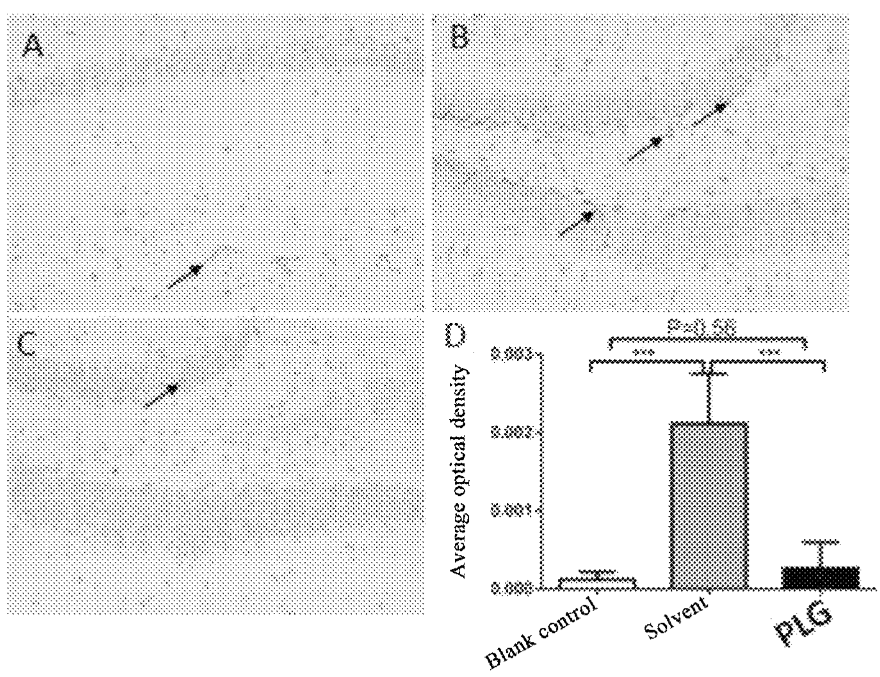
FIG. 7A to FIG. 7D show immunohistochemical staining results of GFAP in the hippocampus of a mouse model of Huntington's disease after 7 days of plasminogen administration. A shows a blank control group, B shows a solvent control group, C shows a plasminogen administration group, and D shows quantitative analysis results of the average optical density. The results show that a certain amount of GFAP is expressed in the hippocampus of a mouse of the blank control group; the expression of GFAP in the hippocampus of a mouse of the solvent control group is obviously higher than that of the mouse of the blank control group, and the statistical difference is extremely significant (*** indicates P<0.001); the expression of GFAP in the hippocampus of a mouse of the plasminogen administration group is obviously lower than that of the mouse of the solvent control group, the statistical difference is extremely significant, and there is no statistical difference between the mice of the plasminogen administration group and the blank control group in the expression of GFAP in the hippocampus. The results indicate that plasminogen can reduce the expression of GFAP in the hippocampus of the mouse model of Huntington's disease, inhibit the proliferation of astrocytes, improve the recovery of hippocampal damage.

The results show that a certain amount of GFAP is expressed in the hippocampus of the mouse of the blank control group (see FIG. 7A); the expression of GFAP in the hippocampus of the mouse of the solvent control group (see FIG. 7B) is obviously higher than that of the mouse of the blank control group, and the statistical difference is extremely significant (* indicates P<0.001) (see FIG. 7D); the expression of GFAP in the hippocampus of the mouse of the plasminogen administration group (see FIG. 7**C) is obviously lower than that of the mouse of the solvent control group, the statistical difference is significant, and there is no statistical difference between the mice of the plasminogen administration group and the blank control group in the expression of GFAP in the hippocampus. The results indicate that plasminogen can reduce the expression of GFAP in the hippocampus of the mouse model of Huntington's disease, can inhibit the proliferation of astrocytes, and has neuroprotective effects.

Example 4 Plasminogen Reduces Apoptosis of Hippocampal Cells in a Mouse Model of Huntington's Disease 3 days before model construction, 6-week-old male C57 mice were weighed and subjected to a simple open field test.

The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, and the hippocampus was taken out and fixed in a 10% neutral formaldehyde solution for 24-48 h. The fixed hippocampus tissue was dehydrated with graded ethanol, cleared with xylene, and embedded in paraffin. The tissue was cut into slices with a thickness of 3 μm, and the slice was subjected to deparaffinage and rehydration, and washed once with water. The tissue slice was marked by using a PAP pen, incubated in 3% hydrogen peroxide for 15 min, and washed twice with 0.01 M PBS for 5 min each time. The slice was blocked with a 5% normal goat serum (Vector laboratories, Inc., USA) for 30 min; and then, the goat serum was removed, a rabbit anti-caspase-3 antibody (Boster Biological Technology, BA2142) was added dropwise, and the slice was incubated at 4° C. overnight and washed twice with 0.01 M PBS for 5 min each time. A goat anti-rabbit IgG (HRP) antibody (Abcam) secondary antibody was added, and the slice was incubated at the room temperature for 1 h and washed twice with 0.01 M PBS for 5 min each time. The slice was developed by using a DAB kit (Vector laboratories, Inc., USA), washed three times with water, restained with hematoxylin for 30 s, and rinsed with running water for 5 min. The stained slice was dehydrated with graded ethanol, cleared with xylene, sealed by a neutral gum, and observed under a 400× optical microscope.

The caspase family plays a very important role in mediating apoptosis, with caspase-3 being a key executive molecule, which functions in many apoptosis signaling pathways. In a model of 3-NP Huntington's disease, neuronal apoptosis is increased and the expression of caspase-3 is up-regulated.

Figure 8:
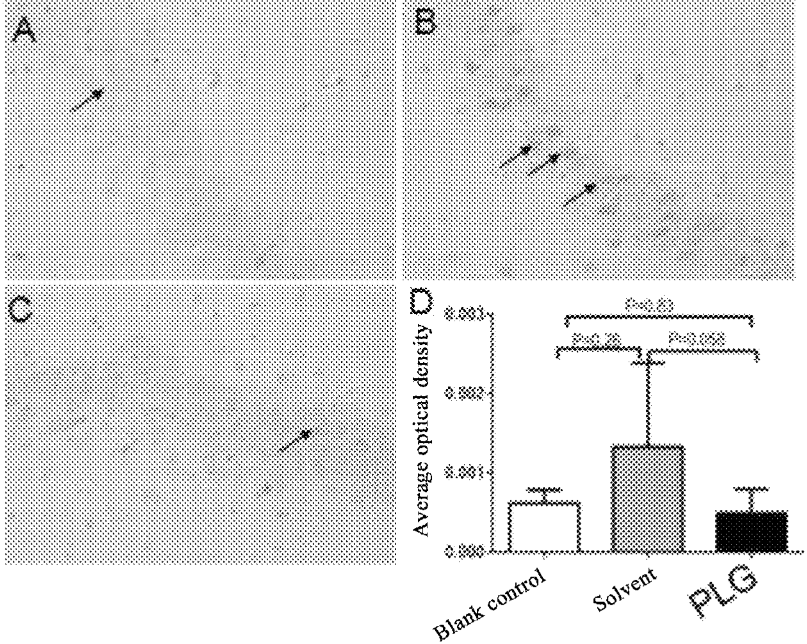
FIG. 8A to FIG. 8D show immumohistochemical staining results of caspase-3 in the hippocampus of a mouse model of Huntington's disease after 7 days of plasminogen administration. A shows a blank control group, B shows a solvent control group, C shows a plasminogen administration group, and D shows quantitative analysis results of the average optical density. The results show that a certain amount of caspase-3 (indicated by arrows) is expressed in the hippocampus of a mouse of the blank control group; the expression of caspase-3 in the hippocampus of a mouse of the solvent control group is obviously increased; the expression of caspase-3 in the hippocampus of a mouse of the plasminogen administration group is obviously lower than that of the mouse of the solvent control group, and the statistical difference is close to significant (P=0.058). The results indicate that plasminogen can reduce the expression of caspase-3 and reduce apoptosis of hippocampal cells in the mouse model of Huntington's disease.

The results show that a certain amount of caspase-3 (indicated by arrows) is expressed in the hippocampus of the mouse of the blank control group (see FIG. 8A); the expression of caspase-3 in the hippocampus of the mouse of the solvent control group (see FIG. 8B) is obviously increased; the expression of caspase-3 in the hippocampus of the mouse of the plasminogen administration group (see FIG. 8C) is obviously less than that of the mouse of the solvent control group, and the statistical difference is close to significant (P=0.058) (see FIG. 8D). The results indicate that plasminogen can reduce the expression of caspase-3 and reduce apoptosis of hippocampal cells in the mouse model of Huntington's disease.

Example 5 Plasminogen Promotes the Recovery of the Number of Nissl Bodies in Cerebellar Neurons in a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, the cerebellum was taken out and fixed in a 10% neutral formaldehyde solution for 24-48 h. The fixed cerebellum was dehydrated with degraded ethanol, cleared with xylene, and embedded in paraffin. The tissue was cut into slices with a thickness of 3 μm, and the slice was subjected to deparaffinage and rehydration, and stained with a 0.5% toluidine blue dye. The stained slice was dehydrated with graded ethanol, cleared with xylene, and sealed by a neutral gum. The slice was observed and photographed under an optical microscope.

Nissl bodies are one of characteristic structures of neurons and are synthesis site of structural proteins and functional proteins of neurons, and their quantity and distribution are closely related to the functional state of neurons. Main chemical components of a Nissl body are ribonucleic acid and protein, Nissl bodies also called extranuclear chromatin and have affinity to basic dyes such as toluidine blue, thionine, and cresyl violet. Toluidine blue staining is the most commonly used conventional method for developing Nissl bodies[8]. When a nervous system disease occurs, the state of Nissl bodies will be abnormal.

Figure 9:
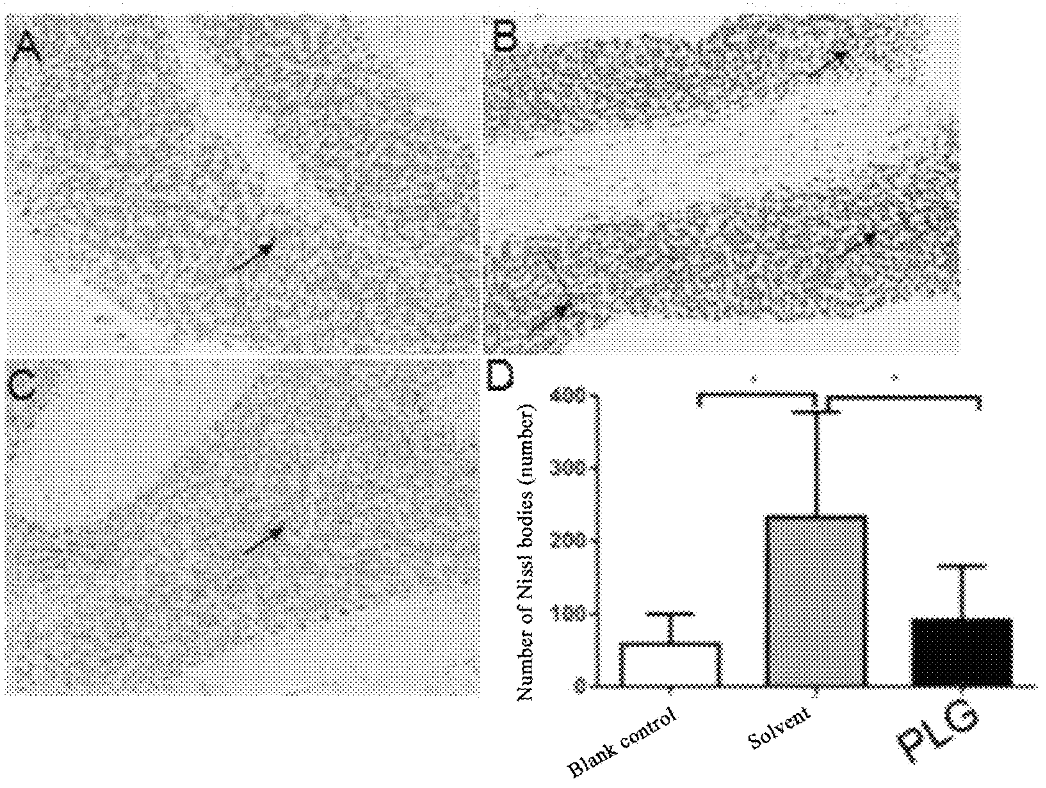
FIG. 9A to FIG. 9D show toluidine blue staining results of the cerebellum of a mouse model of Huntington's disease after 7 days of plasminogen administration. A shows a blank control group, B shows a solvent control group, C shows a plasminogen administration group, and D shows analysis results of the number of Nissl bodies in the cerebellum. The results show that a certain number of Nissl bodies (indicated by arrows) are present in cerebellar neurons in a mouse of the blank control group; the number of Nissl bodies in cerebellar neurons in a mouse of the solvent control group is obviously greater than that in the mouse of the blank control group; the number of Nissl bodies in cerebellar neurons in a mouse of the plasminogen administration group is obviously less than that in the mouse of the solvent control group, the statistical difference is significant (* indicates $P<0.05$), and there is no obvious difference between the mice of the plasminogen administration group and the blank control group. The results indicate that plasminogen can promote the recovery of the number of Nissl bodies in the cerebellar neurons in the mouse model of Huntington's disease.

The results show that a certain number of Nissl bodies (indicated by arrows) are present in cerebellar neurons in the mouse of the blank control group (see FIG. 9A); the number of Nissl bodies in cerebellar neurons in the mouse of the solvent control group (see FIG. 9B) is obviously greater than that in the mouse of the blank control group; the number of Nissl bodies in cerebellar neurons in the mouse of the plasminogen administration group (see FIG. 9C) is obviously less than that in the mouse of the solvent control group, the statistical difference is significant (* indicates $P<0.05$) (see FIG. 9D), and there is no obvious difference between the mice of the plasminogen administration group and the blank control group in the number of Nissl bodies in cerebellar neurons. The results indicate that plasminogen cam promote the recovery of the number of Nissl bodies in cerebellar neurons of the mouse model of Huntington's disease.

Example 6 Plasminogen Promotes the Recovery of the Number of Nissl Bodies in Hippocampal Neurons in a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, and the hippocampus was taken out and fixed in a 10% neutral formaldehyde solution for 24-48 h. The fixed hippocampus tissue was dehydrated with graded ethanol, cleared with xylene, and embedded in paraffin. The tissue was cut into slices with a thickness of 3 μm, and the slice was subjected to deparaffinage and rehydration, and stained with a 0.4% cresyl violet dye (pH=3, manufacturer: Sinopharm Chemical Reagent Co., Ltd., batch number: 20181019). The stained slice was dehydrated with graded ethanol, cleared with xylene, and sealed by a neutral gum. The slice was observed and photographed under a 400× optical microscope.

Cresyl violet staining uses cresyl violet as a core dye. Cresyl violet has a photosensitive effect and can well show changes of Nissl bodies.

Figure 10:
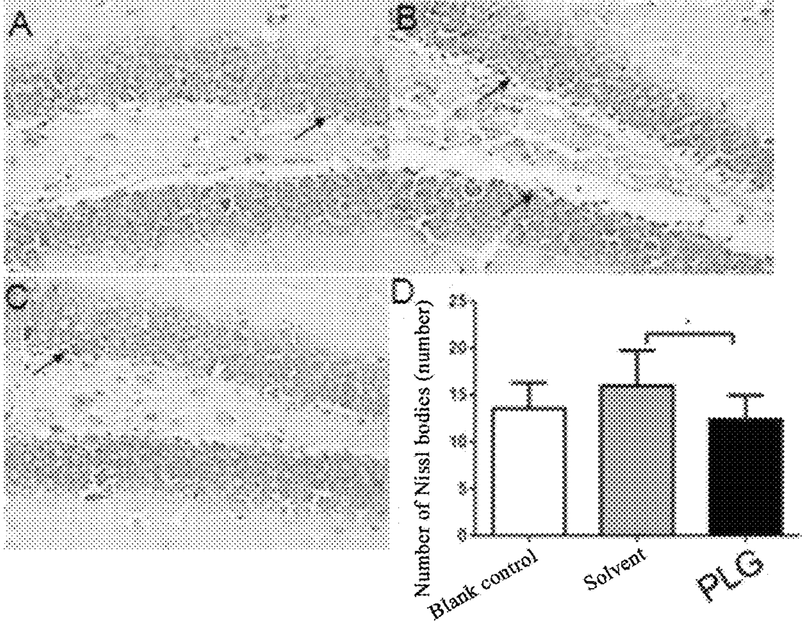
FIG. 10A to FIG. 10D show cresyl violet staining results of the left hippocampus of a mouse model of Huntington's disease after 7 days of plasminogen administration. A shows a blank control group, B shows a solvent group, C shows a plasminogen administration group, and D shows analysis results of the number of Nissl bodies in the hippocampus. The results show that a certain number of Nissl bodies (indicated by arrows) are present in left hippocampal neurons in a mouse of the blank control group; the number of Nissl bodies in left hippocampal neurons in a mouse of the solvent group is obviously greater than that in the mouse of the blank control group; the number of Nissl bodies in left hippocampal neurons in a mouse of the plasminogen administration group is obviously less than that in the mouse of the solvent group, and the statistical difference is significant (* indicates $P<0.05$). The results indicate that plasminogen can promote the recovery of the number of Nissl bodies in the hippocampal neurons.

The results show that a certain number of Nissl bodies (indicated by arrows) are present in the left hippocampus of the mouse of the blank control group (see FIG. 10A); the number of Nissl bodies in the left hippocampus of the mouse of the solvent group (see FIG. 10B) is obviously greater than that of the mouse of the blank control group; the number of Nissl bodies in the left hippocampus of the mouse of the plasminogen administration group (see FIG. 10C) is obviously less than that of the mouse of the solvent group, and the statistical difference is significant (* indicates $P<0.05$) (see FIG. 10D). The results indicate that plasminogen can promote the recovery of the number of Nissl bodies in hippocampal neurons.

Example 7 Plasminogen Promotes the Recovery of the Number of Nissl Bodies in Striatal Neurons in a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, the striatum was taken out and fixed in a 10% neutral formaldehyde solution for 24-48 h. The fixed striatum tissue was dehydrated with graded ethanol, cleared with xylene, and embedded in paraffin. The tissue was cut into slices with a thickness of 3 μm, and the slice was subjected to deparaffinage and rehydration, and stained with a 0.4% cresyl violet dye (pH=3). The stained slice was dehydrated with graded ethanol, cleared with xylene, and sealed by a neutral gum. The slice was observed and photographed under a 400× optical microscope.

Figure 11:
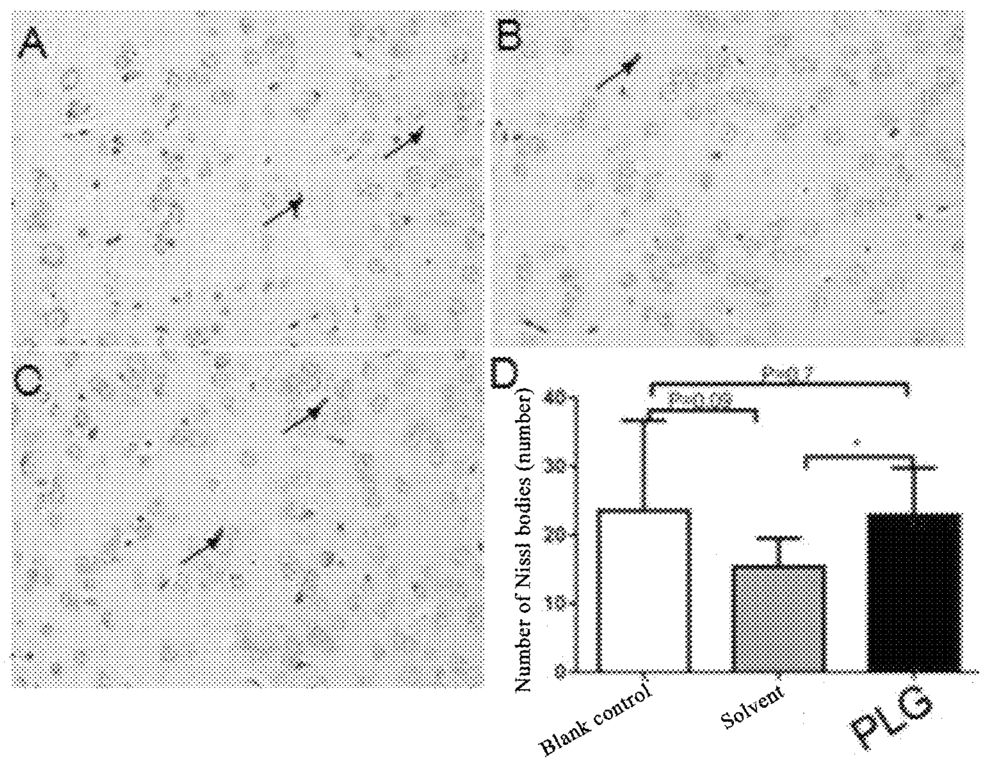
FIG. 11A to FIG. 11D show cresyl violet staining results of the striatum of a mouse model of Huntington's disease after 7 days of plasminogen administration. A shows a blank control group, B shows a solvent control group, C shows a plasminogen administration group, and D shows analysis results of the number of Nissl bodies in the striatum. The results show that a certain number of Nissl bodies (indicated by arrows) are present in striatal neurons in a mouse of the blank control group; the number of Nissl bodies in striatal neurons in a mouse of solvent group is obviously less than that in the mouse of the blank control group; the number of Nissl bodies in striatal neurons in a mouse of the plasminogen administration group is obviously greater than that in the mouse of solvent group, and the statistical difference is significant (* indicates $P<0.05$). The results indicate that plasminogen can promote the recovery of the number of Nissl bodies in the striatal neurons.

The results show that a certain number of Nissl bodies are present in striatal neurons in the mouse of the blank control group (see FIG. 11A); the number of Nissl bodies in striatal neurons in the mouse of the solvent group (see FIG. 11B) is obviously less than that of the mouse of the blank control group; the number of Nissl bodies in striatal neurons in the mouse of the plasminogen administration group (see FIG. 11C) is obviously greater than that of the mouse of the solvent group, and the statistical difference is significant (* indicates $P<0.05$) (see FIG. 11D). The results indicate that plasminogen can promote the recovery of the number of Nissl bodies in the striatal neurons.

Example 8 Plasminogen Reduces Hippocampal Damage in a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, the hippocampus was taken out and fixed in a 10% formaldehyde solution for 24-48 h. The fixed hippocampus tissue was dehydrated with graded ethanol, cleared with xylene, and embedded in paraffin. The tissue was cut into slices with a thickness of 4 μm, and the slice was subjected to deparaffinage and rehydration, stained with hematoxylin and eosin (HE staining), differentiated with 1% hydrochloride ethanol, returned to blue with ammonia water, dehydrated with graded ethanol, sealed, and observed under a 200× optical microscope.

Figure 12:
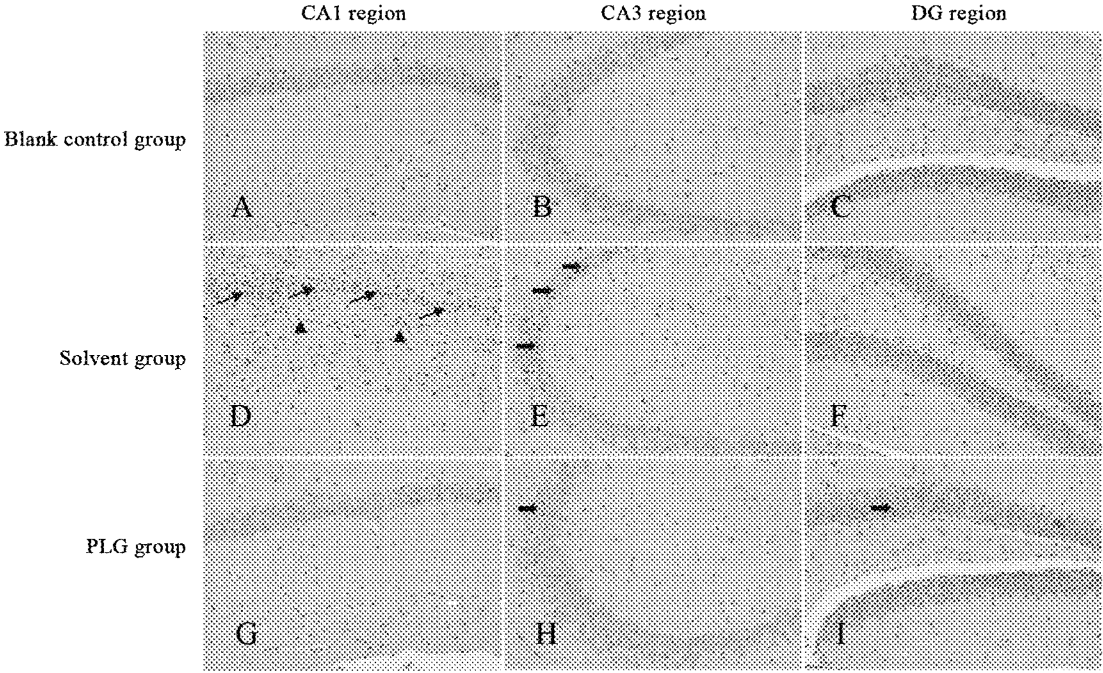
FIG. 12A to FIG. 12I are H&E staining results of the hippocampus of a mouse model of Huntington's disease after 7 days of plasminogen administration. A, B, and C show a blank control group, D, E, and F show a solvent control group, and G, H, and I show a plasminogen administration group. The result show that the overall morphology of the hippocampus of a mouse of the blank control group is normal, and the structure is intact; there are disorganized neuronal arrangement, atrophy of nerve cells (indicated by thin arrows), cellular degeneration and necrosis, and sparse and edematous surrounding brain tissue (indicated by triangles) in the CA1 region, and multiple pyknotic and hyperchromatic neuronal nuclei (indicated by thick arrows) in the CA3 region of the hippocampus of a mouse of the solvent control group; the morphology of the regions of the hippocampus of a mouse of the plasminogen administration group is restored, and there are some pyknotic and hyperchromatic neuronal nuclei in the CA3 region and the DG region. The results indicate that plasminogen can repair hippocampal damage in the mouse model of Huntington's disease.

The results show that the overall morphology of the hippocampus of the mouse of the blank control group (see FIG. 12A to FIG. 12C), and the structure is intact; there are disorganized neuronal arrangement, atrophy of nerve cells (indicated by thin arrows), cellular degeneration and necrosis, and sparse and edematous surrounding brain tissue (indicated by triangles) in the CA1 region, and multiple pyknotic and hyperchromatic neuronal nuclei (indicated by thick arrows) in the CA3 region of the hippocampus of the mouse of the solvent control group (see 12D to FIG. 12F); the morphology of the regions of the hippocampus of the mouse of the plasminogen administration (see FIG. 12G to FIG. 12I) group is restored, and there are some pyknotic and hyperchromatic neuronal nuclei in the CA3 region and the DG region. The results indicate that plasminogen can repair hippocampal damage in the mouse model of Huntington's disease.

Example 9 Plasminogen Reduces Striatal Damage in a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, the striatum was taken out and fixed in a 10% neutral formaldehyde solution for 24-48 h. The fixed striatum tissue was dehydrated with graded ethanol, cleared with xylene, and embedded in paraffin. The tissue was cut into slices with a thickness of 3 μm, and the slice was subjected to deparaffinage and rehydration, stained with hematoxylin and eosin (HE staining), differentiated with 1% hydrochloride ethanol, returned to blue with ammonia water, dehydrated with graded ethanol, sealed, and observed under a 200× optical microscope.

Figure 13:
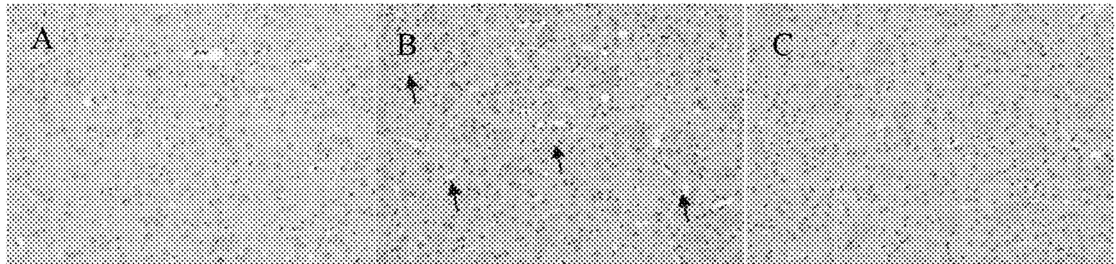
FIG. 13A to FIG. 13C show H&E staining results of the striatum of a mouse model of Huntington's disease after 7 days of plasminogen administration. A shows a blank control group, B shows a solvent control group, and C shows a plasminogen administration group. The results show that the morphological structure of the striatum of a mouse of the blank control group is normal; striatal neurons in a mouse of the solvent group are degenerated, some cell nuclei (indicated by arrows) are vacuolated, and the arrangement of brain cells is disorganized; the overall structure of the striatum of a mouse of the plasminogen administration group is significantly improved, and is similar to that of the mouse of the blank control group. The results indicate that plasminogen can repair striatal damage in the mouse model of Huntington's disease.

The results show that the structural morphology of the striatum of the mouse of the blank control group (see FIG. 13A) is normal; striatal neurons in the mouse of the solvent group (see FIG. 13B) are degenerated, some cell nuclei (indicated by arrows) are vacuolated, and the arrangement of brain cells is disordered; the overall structure of the striatum of the mouse of the plasminogen administration group (see FIG. 13C) is significantly improved, and is similar to that of the mouse of the blank control group. The results indicate that plasminogen can repair striatal damage in the mouse model of Huntington's disease.

Example 10 Plasminogen Improves Olfactory Nodule Damage in a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, and the brain tissue was taken out and fixed in a 10% neutral formaldehyde solution for 24-48 h. The fixed brain tissue was dehydrated with graded ethanol, cleared with xylene, and embedded in paraffin. The tissue was cut into slices with a thickness of 3 μm, the slice was subjected to deparaffinage and rehydration, stained with hematoxylin and eosin (HE staining), differentiated with 1% hydrochloride ethanol, returned to blue with ammonia water, dehydrated with graded ethanol, sealed, and placed under a 200× optical microscope, and the olfactory tubercle was observed.

It has been reported that the olfactory tubercle of the mouse model of Huntington's disease is damaged, and patients with Huntington's disease have olfactory deficits[9].

Figure 14:
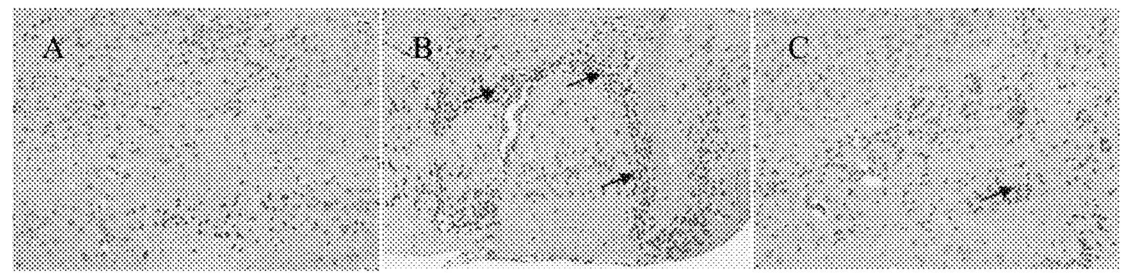
FIG. 14A to FIG. 14C show H&E staining results of the olfactory tubercle of a mouse model of Huntington's disease after 7 days of plasminogen administration. A shows a blank control group, B shows a solvent control group, and C shows a plasminogen administration group. The results show that the morphological structure of the olfactory tubercle of a mouse of the blank control group is normal; glial cell infiltration (indicated by arrows) in the olfactory tubercle of a mouse of the solvent group is severe; and glial cell infiltration in the olfactory tubercle of a mouse of the plasminogen administration group is obviously milder than that of the mouse of the solvent group. The results indicate that plasminogen can improve olfactory tubercle damage in the brain of the mouse model of Huntington's disease.

The results show that the structural morphology of the olfactory tubercle in the brain of the mouse of the blank control group (see FIG. 14A) is normal; glial cell infiltration (indicated by arrows) in the olfactory tubercle of the mouse of the solvent group (see FIG. 14B) is severe; and glial cell infiltration in the olfactory tubercle of the mouse of the plasminogen administration (see FIG. 14C) group is obviously milder than that of the mouse of the solvent group. The results indicate that plasminogen can improve olfactory tubercle damage in the brain of the mouse model of Huntington's disease.

Example 11 Plasminogen Promotes the Expression of BDNF in the Hippocampus of a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, and the hippocampus was taken out and fixed in a 10% neutral formaldehyde solution for 24-48 h. The fixed hippocampus tissue was dehydrated with graded ethanol, cleared with xylene, and embedded in paraffin. The tissue was cut into slices with a thickness of 3 μm, and the slice was subjected to deparaffinage and rehydration, and washed once with water. The tissue slice was marked by using a PAP pen, incubated in 3% hydrogen peroxide for 15 min, and washed twice with 0.01 M PBS for 5 min each time. The slice was blocked with a 5% normal goat serum (Vector laboratories, Inc., USA) for 30 min; and then, the goat serum was removed, a rabbit anti-BNDF antibody (Boster Biological Technology, PB9075) was added dropwise, and the slice was incubated at 4° C. overnight and washed twice with 0.01 M PBS for 5 min each time. A goat anti-rabbit IgG (HRP) antibody (Vector laboratories, MP-7451) secondary antibody was added, and the slice was incubated at the room temperature for 30 min and washed twice with 0.01 M PBS for 5 min each time. The slice was developed by using a DAB kit (Vector laboratories, Inc., USA), washed three times with water, restained with hematoxylin for 30 s, and rinsed with running water for 5 min. The stained slice was dehydrated with graded ethanol, cleared with xylene, sealed by a neutral gum, and observed under a 400× optical microscope.

Brain-derived neurotrophic factor (BDNF) is a protein synthesized in the brain, is abundant in the central nervous system, and plays an important role in the survival, differentiation, and growth and development of neurons during the development of the central nervous system. BDNF can prevent neuronal damage and death, improve the pathological state of neurons, and promote biological effects, such as regeneration and differentiation, of damaged neurons[10].

Figure 15:
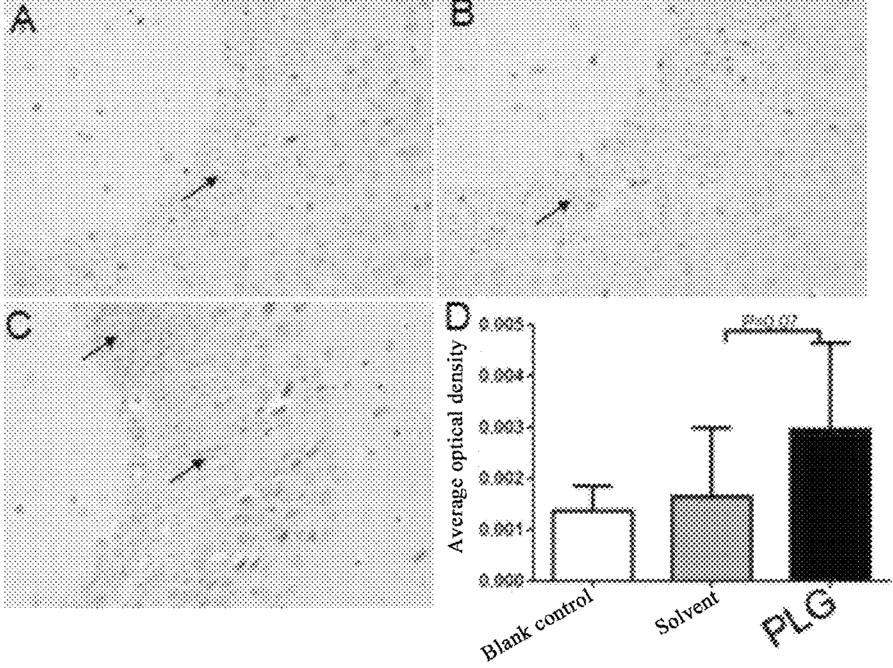
FIG. 15A to FIG. 15D show immumohistochemical staining results of BDNF in the hippocampus of a mouse model of Huntington's disease after 7 days of plasminogen administration. A shows a blank control group, B shows a solvent control group, C shows a plasminogen administration group, and D shows quantitative analysis results of the average optical density. The results show that a certain amount of BDNF (indicated by arrows) is expressed in the right hippocampus of a mouse of the blank control group; the expression of BDNF in the right hippocampus of a mouse of the solvent group is slightly higher than that of the mouse of the blank control group; the expression of BDNF in the right hippocampus of a mouse of the plasminogen administration group is obviously higher than that of the mouse of the solvent group, and the statistical difference is close to significant ($P=0.07$). The results indicate that damage can stimulate the expression of BDNF, but plasminogen can further promote the expression of BDNF, so as to promote the repair of hippocampal damage in the mouse model of Huntington's disease.

The results show that a certain amount of BDNF (indicated by arrows) is expressed in the right hippocampus of the mouse of the blank control group (see FIG. 15A); the expression of BDNF in the right hippocampus of the mouse of the solvent group (see FIG. 15B) is slight higher than that of the mouse of the blank control group; the expression of BDNF in the right hippocampus of the mouse of the plasminogen administration group (see FIG. 15C) is obviously higher than that of the mouse of the solvent group, and the statistical difference is close to significant (P=0.07) (see FIG. 15D). The results indicate that damage can stimulate the expression of BDNF, but plasminogen can further promote the expression of BDNF, so as to promote the repair of hippocampal damage in the mouse model of Huntington's disease.

Example 12 Plasminogen Promotes the Expression of BDNF in the Striatum of a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, the striatum was taken out and fixed in a 10% neutral formaldehyde solution for 24-48 h. The fixed striatum tissue was dehydrated with graded ethanol, cleared with xylene, and embedded in paraffin. The tissue was cut into slices with a thickness of 3 μm, and the slice was subjected to deparaffinage and rehydration, and washed once with water. The tissue slice was marked by using a PAP pen, incubated in 3% hydrogen peroxide for 15 min, and washed twice with 0.01 M PBS for 5 min each time. The slice was blocked with a 5% normal goat serum (Vector laboratories, Inc., USA) for 30 min; and then, the goat serum was removed, a rabbit anti-BNDF antibody (Boster Biological Technology, PB9075) was added dropwise, and the slice was incubated at 4° C. overnight and washed twice with 0.01 M PBS for 5 min each time. A goat anti-rabbit IgG (HRP) antibody (Vector laboratories, MP-7451) secondary antibody was added, and the slice was incubated at the room temperature for 30 min and washed twice with 0.01 M PBS for 5 min each time. The slice was developed by using a DAB kit (Vector laboratories, Inc., USA), washed three times with water, restained with hematoxylin for 30 s, and rinsed with running water for 5 min. The stained slice was dehydrated with graded ethanol, cleared with xylene, sealed by a neutral gum, and observed under a 400× optical microscope.

Figure 16:
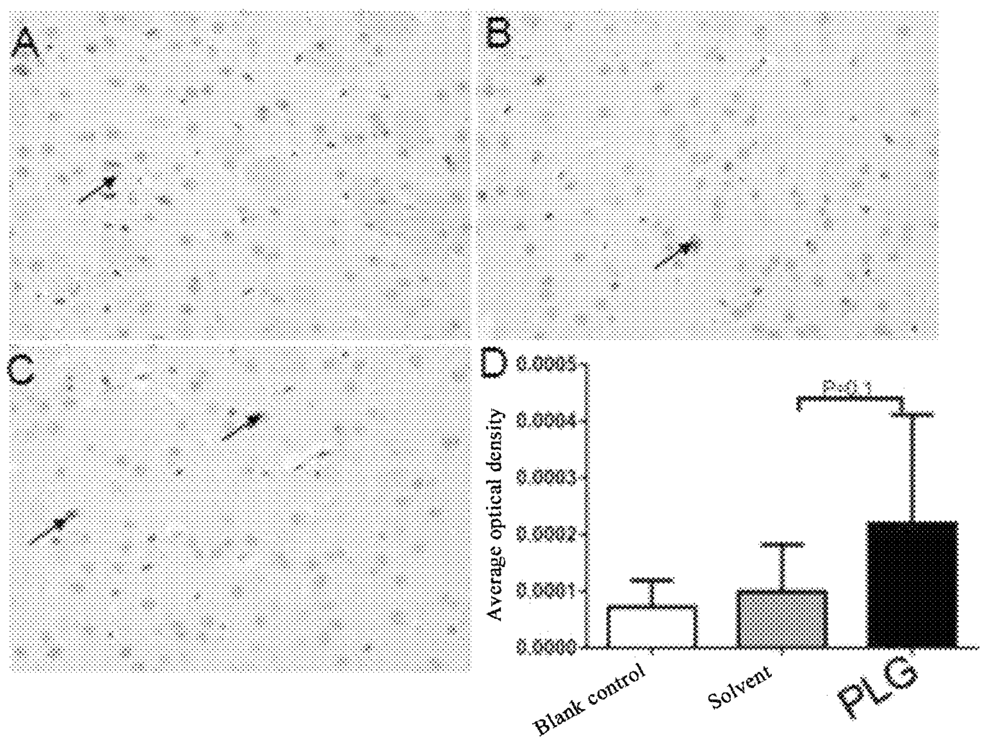
FIG. 16A to FIG. 16D show immumohistochemical staining results of BDNF in the striatum of a mouse model of Huntington's disease after 7 days of plasminogen administration. A shows a blank control group, B shows a solvent control group, C shows a plasminogen administration group, and D shows quantitative analysis results of the average optical density. The results show that a certain amount of BDNF (indicated by arrows) is expressed in the striatum of a mouse of the blank control group; the expression of BDNF in the striatum of a mouse of the solvent group is slightly higher than that of the mouse of the blank control group; the expression of BDNF in the striatum of a mouse of the plasminogen administration group is obviously higher than that of the mouse of the solvent group, and the statistical difference is close to significant (P=0.1). The results indicate that damage can stimulate the expression of BDNF, but plasminogen can further promote the expression of BDNF, so as to promote of the repair of striatal damage in the mouse model of Huntington's disease.

The results show that a certain amount of BDNF (indicated by arrows) is expressed in the striatum of the mouse of the blank control group (see FIG. 16A); the expression of BDNF in the striatum of the mouse of the solvent group (see FIG. 16B) is slightly higher than that of the mouse of the blank control group; the expression of BDNF in the striatum of the mouse of the plasminogen administration group (see FIG. 16C) is obviously higher than that of the mouse of the solvent group, and the statistical difference is close to significant (P=0.1) (see FIG. 16D). The results indicate that damage can stimulate the expression of BDNF, but plasminogen can further promote the expression of BDNF, so as to promote of the repair of striatal damage in the mouse model of Huntington's disease.

Example 13 Plasminogen Promotes the Regeneration of the Striatal Myelin Sheath in a Mouse Model of Huntington's Disease 3 days before model construction, 6-week-old male C57 mice were weighed and subjected to a simple open field test. The mice were observed for 5 min, spontaneous differences in the random animals were excluded, and finally 23 experimental animals were selected. The mice were randomly divided into two groups, i.e., a blank control group and a model group, according to total travel distances of the mice in the open field test, 6 mice in the blank control group and 17 mice in the model group. 125 μL of PBS was intraperitoneally injected into each mouse of the blank control group, and a 3-nitropropionic acid (3-NP) solution was intraperitoneally injected into each mouse of the model group at a dose of 50 mg/kg (by body weight), twice a day (every 12 h), for 5 consecutive days, to construct models of Huntington's disease[1]. Preparation of the 3-NP solution: 3-NP powder (Sigma, catalog number: N5636) was dissolved in PBS to a concentration of 10 mg/mL. On the second day after model construction was completed, which was defined as day 0 of administration, all the mice were weighed and subjected to an open field test. The mice of the model group were randomly divided into two groups, i.e., a solvent control group (9 mice) and a plasminogen administration group (8 mice), according to total travel distances of the mice in the open field test. A solvent (a 10 mM citric acid-sodium citrate solution, pH=7.4) was injected to each mouse of the solvent control group via the tail vein at a dose of 0.1 mL/day, human plasminogen was injected into each mouse of the plasminogen administration group via the tail vein at a dose of 1 mg/0.1 mL/day, and administration was performed for 7 consecutive days. The mice were killed on day 7 of administration, the striatum was taken out and fixed in a 10% neutral formaldehyde solution for 24-48 h. The fixed striatum tissue was dehydrated with graded ethanol, cleared with xylene, and embedded in paraffin. The spinal cord tissue was transversely cut into slices with a thickness of 4 μm, and the slice was subjected to deparaffinage and rehydration, and subjected to LFB staining with a myelin sheath dye. The stained slice was dehydrated with graded ethanol, cleared with xylene, and sealed by a neutral gum. The slice was observed and photographed under an optical microscope.

Luxol fast blue (LFB) staining uses luxol fast blue to stain the myelin sheath, and is an effective method for studying corticospinal tract positioning and myelin sheath lesions, and observing damage to and regeneration and repair of the morphology[11-12].

Figure 17:
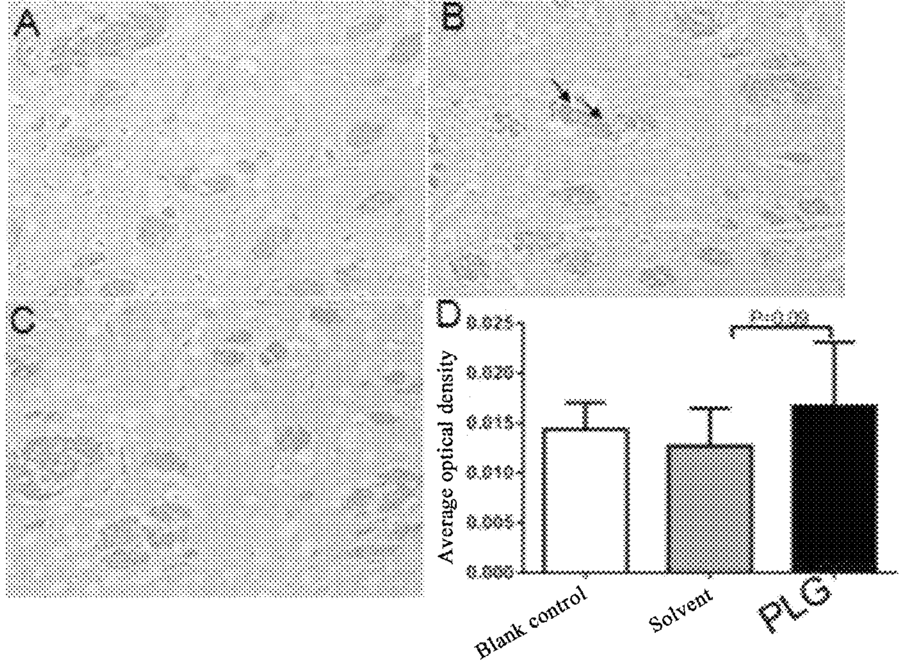
FIG. 17A to FIG. 17D show LFB staining results of the striatum of a mouse model of Huntington's disease after 7 days of plasminogen administration. A shows a blank control group, B shows a solvent control group, C shows a plasminogen administration group, and D shows quantitative analysis results of the average optical density. The results show that the structure of the striatal myelin sheath of a mouse of the blank control group is normal; the striatal myelin protein content in a mouse of the solvent group is decreased, and cavitation (indicates by arrows) can be observed; the striatal myelin protein content in a mouse of the plasminogen administration group is obviously greater than that in the mouse of the solvent group, and the statistical difference is close to significant (P=0.09). The results indicate that plasminogen can promote the formation of striatal myelin protein in the mouse model of Huntington's disease.

The results show that the structure of the striatal myelin sheath of the mouse of the blank control group (see FIG. 17A) is normal; the striatal myelin protein content in the mouse of the solvent group (see FIG. 17B) is decreased, and cavitation (indicates by arrows) can be observed; the striatal myelin protein content in the mouse of the plasminogen administration group (see FIG. 17C) is obviously greater than that in the mouse of the solvent group, and the statistical difference is close to significant (P=0.09) (see FIG. 17D). The results indicate that plasminogen can promote the formation of striatal myelin protein in the mouse model of Huntington's disease.

REFERENCES

[1] Wang L, Wang J, Yang L, et al. Effect of Praeruptorin C on 3-nitropropionic acid induced Huntington's disease-like symptoms in mice [J]. Biomedicine & Pharmacotherapy, 2017, 86: 81-87.

[2] Marchei P, Diverio S, Falocci N, et al. Breed differences in behavioural development in kittens [J]. Physiology & Behavior, 2009, 96 (4-5): 522-531.
[3] Jacob W, Yassouridis A, Marsicano G, et al. Endocannabinoids render exploratory behaviour largely independent of the test aversiveness: role of glutamatergic transmission [J]. Genes Brain & Behavior, 2010, 8 (7): 685-698.
[4] Walz K, Spencer C, Kaasik K, et al. Behavioral characterization of mouse models for Smith-Magenis syndrome and dup (17) (p11.2 p11.2) [J]. Human Molecular Genetics, 2004, 13 (4): 367.
[5] Aziz N A, Burg J M M V D, Landwehrmeyer G B, et al. Weight loss in Huntington disease increases with higher CAG repeat number [J]. Neurology, 2009, 73 (7): 1506.
[6] Hol E M, Pekny M. Glial fibrillary acidic protein (GFAP) and the astrocyte intermediate filament system in diseases of the central nervous system [J]. Current Opinion in Cell Biology, 2015, 32 (1): 121-130.
[7] Vagner T, Dvorzhak A, Wójtowicz A M, et al. Systemic application of AAV vectors targeting GFAP-expressing astrocytes in Z-Q175-KI Huntington's disease mice [J]. Molecular & Cellular Neuroscience, 2016, 77: 76-86.
[8] Xie J X, Feng Y, Yuan J M, et al. Positive effects of bFGF modified rat amniotic epithelial cells transplantation on transected rat optic nerve [J]. Plos One, 2014, 10 (3): e0119119.
[9] Kohl Z, Regensburger M, Aigner R, et al. Impaired adult olfactory bulb neurogenesis in the R6/2 mouse model of Huntington's disease [J]. BMC Neuroscience, 11, 1 (2010-09-13), 2010, 11 (1): 114.
Hyman C, Hofer M, Barde Y A, et al. BDNF is a neurotrophic factor for dopaminergic neurons of the substantia nigra [J]. Nature, 1991, 350 (6315): 230-232.
Sun S W, Liang H F, Trinkaus K et al. Noninvasive detection of cuprizone induced axonal damage and demyelination in the mouse corpus callosum. Magn Reson Med. 2006 February; 55 (2): 302-8.
Vallières N1, Berard J L, David S et al. Systemic injections of lipopolysaccharide accelerates myelin phagocytosis during Wallerian degeneration in the injured mouse spinal cord. Glia. 2006 Jan. 1; 53 (1): 103-13.

What is claimed is:

1. A method for treating Huntington's disease, comprising administering a therapeutically effective amount of plasminogen to a subject with Huntington's disease, wherein the plasminogen is the only active ingredient for said treatment, wherein treating Huntington's disease comprises alleviating one or more of a) a movement disorders, b) cognitive impairment, or c) a neuropsychiatric symptom that is associated with Huntington's disease, wherein the movement disorder associated with Huntington's disease comprises a voluntary movement disorder or an involuntary movement disorder wherein the plasminogen comprises an amino acid sequence as set forth in SEQ ID NO: 2, 6, 8, 10, 12, or 14.

2. The method according to claim 1, wherein the plasminogen has one or more effects on the subject with Huntington's disease, the one or more effects being selected from: improvement or relief of movement disorders, improvement of cognitive impairment, deceleration of weight loss, promotion of the repair of damaged neurons, improvement of neuropsychiatric symptoms, relief of anxiety, reduction of the expression of glial fibrillary acidic protein (GFAP) in the hippocampus, reduction of apoptosis of hippocampal cells, promotion of recovery of the number of Nissl bodies in cerebellar, hippocampal or striatal neurons, repair of damage to the hippocampus, striatum or olfactory tubercle, promotion of the expression of brain-derived neurotrophic factor (BDNF) in the hippocampus or striatum, and promotion of the regeneration of striatal myelin sheaths.

3. A method for treating Huntington's disease, comprising administering a therapeutically effective amount of plasminogen to a subject with Huntington's disease, wherein the plasminogen is used in combination with one or more other drugs or treatment methods, wherein the other drugs or treatment methods are selected from one or more of: anti-dopaminergic drugs, dopamine receptor inhibitors, antipsychotic drugs, γ-aminobutyrate transaminase inhibitors, cell transplantation therapy, and gene therapy, wherein treating Huntington's disease comprises alleviating one or more of a) a movement disorders, b) cognitive impairment, or c) a neuropsychiatric symptom that is associated with Huntington's disease, wherein the movement disorder associated with Huntington's disease comprises a voluntary movement disorder or an involuntary movement disorder wherein the plasminogen comprises an amino acid sequence as set forth in SEQ ID NO: 2, 6, 8, 10, 12, or 14.

4. The method according to claim 3, wherein the plasminogen has one or more effects on the subject with Huntington's disease, the one or more effects being selected from: improvement or relief of movement disorders, improvement of cognitive impairment, deceleration of weight loss, promotion of the repair of damaged neurons, improvement of neuropsychiatric symptoms, relief of anxiety, reduction of the expression of glial fibrillary acidic protein (GFAP) in the hippocampus, reduction of apoptosis of hippocampal cells, promotion of recovery of the number of Nissl bodies in cerebellar, hippocampal or striatal neurons, repair of damage to the hippocampus, striatum or olfactory tubercle, promotion of the expression of brain-derived neurotrophic factor (BDNF) in the hippocampus or striatum, and promotion of the regeneration of striatal myelin sheaths.

5. The method according to claim 1, wherein the plasminogen comprises an amino acid sequence as set forth in SEQ ID NO: 2.

6. The method according to claim 1, wherein the plasminogen comprises an amino acid sequence as set forth in SEQ ID NO: 6.

7. The method according to claim 5, wherein the plasminogen comprises an amino acid sequence as set forth in SEQ ID NO: 6.

8. The method according to claim 1, wherein the plasminogen is administered by nasal inhalation, aerosol inhalation, nasal drops, eye drops, ear drops, an intravenous method, an intraperitoneal method, a subcutaneous method, an intracranial method, an intrathecal method, an intra-arterial method or an intramuscular method.

9. The method according to claim 3, wherein the plasminogen comprises an amino acid sequence as set forth in SEQ ID NO: 2.

10. The method according to claim 3, wherein the plasminogen comprises an amino acid sequence as set forth in SEQ ID NO: 6.

11. The method according to claim 9, wherein the plasminogen comprises an amino acid sequence as set forth in SEQ ID NO: 6.

12. The method according to claim 3, wherein the plasminogen is administered by nasal inhalation, aerosol inhalation, nasal drops, eye drops, ear drops, an intravenous method, an intraperitoneal method, a subcutaneous method, an intracranial method, an intrathecal method, an intra-arterial method or an intramuscular method.

13. The method according to claim 1, wherein treating Huntington's disease comprises alleviating the movement disorder, wherein the movement disorder comprises a progressive movement disorder, wherein the progressive movement disorder is characterized by sudden and rapid throbbing or twitching of a limb, face, or trunk that is unpredictable and uncontrollable, or characterized by an uncontrollable slow movement.

14. The method according to claim 1, wherein treating Huntington's disease comprises alleviating the movement disorder, wherein the movement disorder comprises a voluntary movement.

15. The method according to claim 1, wherein treating Huntington's disease comprises alleviating the movement disorder, wherein the movement disorder comprises an involuntary movement.

* * * * *